United States Patent

Okada

(10) Patent No.: US 8,491,466 B2
(45) Date of Patent: Jul. 23, 2013

(54) INTRADUCTAL INSERTION DEVICE

(75) Inventor: Hiromitsu Okada, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 11 days.

(21) Appl. No.: 12/966,438

(22) Filed: Dec. 13, 2010

(65) Prior Publication Data

US 2011/0144434 A1    Jun. 16, 2011

Related U.S. Application Data

(63) Continuation of application No. PCT/JP2010/063040, filed on Aug. 2, 2010.

(30) Foreign Application Priority Data

Sep. 8, 2009   (JP) ................................ 2009-207358

(51) Int. Cl.
  *A61B 1/00*    (2006.01)
  *A61B 1/04*    (2006.01)

(52) U.S. Cl.
  USPC ........................... 600/114; 600/139; 600/101

(58) Field of Classification Search
  USPC .......... 600/114, 109, 160, 101, 139; 606/108; 604/95.03
  See application file for complete search history.

(56) References Cited

U.S. PATENT DOCUMENTS

| | | | |
|---|---|---|---|
| 5,662,587 A * | 9/1997 | Grundfest et al. | 600/114 |
| 6,695,771 B2 * | 2/2004 | Takada | 600/114 |
| 6,824,510 B2 * | 11/2004 | Kim et al. | 600/114 |
| 7,048,717 B1 | 5/2006 | Frassica | |
| 7,736,300 B2 * | 6/2010 | Ziegler et al. | 600/114 |
| 2001/0008952 A1 * | 7/2001 | Takada | 600/155 |
| 2003/0181788 A1 | 9/2003 | Yokoi et al. | |
| 2004/0204702 A1 | 10/2004 | Ziegler et al. | |
| 2005/0251108 A1 * | 11/2005 | Frassica | 604/540 |
| 2007/0055097 A1 * | 3/2007 | Kura et al. | 600/101 |
| 2007/0161862 A1 | 7/2007 | Yokoi et al. | |
| 2007/0167674 A1 * | 7/2007 | Toyama | 600/101 |
| 2007/0167684 A1 * | 7/2007 | Toyama | 600/128 |
| 2007/0173691 A1 | 7/2007 | Yokoi et al. | |
| 2007/0208299 A1 * | 9/2007 | Breedveld | 604/95.03 |

(Continued)

FOREIGN PATENT DOCUMENTS

| | | |
|---|---|---|
| DE | 10 2004 006 855 A1 | 9/2005 |
| DE | 10 2004 012 245 A1 | 9/2005 |

(Continued)

OTHER PUBLICATIONS

Abstract of International Publication No. WO 2004/091689 A2, dated Oct. 28, 2004.

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

An intraductal insertion device includes a thrust generating section installed at an insertion portion. The thrust generating section is made up of a flexible shaft adapted to rotate clockwise or counterclockwise around a shaft axis. The thrust generating section is configured by winding the shaft axis of the flexible shaft around an axis of the insertion portion in an insertion direction.

11 Claims, 13 Drawing Sheets

U.S. PATENT DOCUMENTS

| | | | |
|---|---|---|---|
| 2008/0294008 A1* | 11/2008 | Toyama | 600/139 |
| 2009/0012359 A1 | 1/2009 | Tanaka et al. | |
| 2012/0059210 A1* | 3/2012 | Frassica | 600/3 |

FOREIGN PATENT DOCUMENTS

| | | |
|---|---|---|
| EP | 1 900 318 A1 | 3/2008 |
| FR | 2 481 915 | 11/1981 |
| JP | 55-45427 | 3/1980 |
| JP | 2003-275170 | 9/2003 |
| JP | 2006-523513 | 10/2006 |
| JP | 2006-305320 | 11/2006 |
| JP | 2009-106431 | 5/2009 |
| JP | 2009-254554 | 11/2009 |
| WO | WO 2006/104057 A1 | 10/2006 |

OTHER PUBLICATIONS

International Search Report dated Nov. 2, 2010.
Japanese Office Action of corresponding JP Application No. 2010-547906 dated Feb. 15, 2011 together with an English translation.
Extended Supplementary European Search Report dated Feb. 8, 2013 issued in corresponding Application No. / Patent No. 10815229.9-1660 / 2476452 PCT/JP2010063040.

* cited by examiner

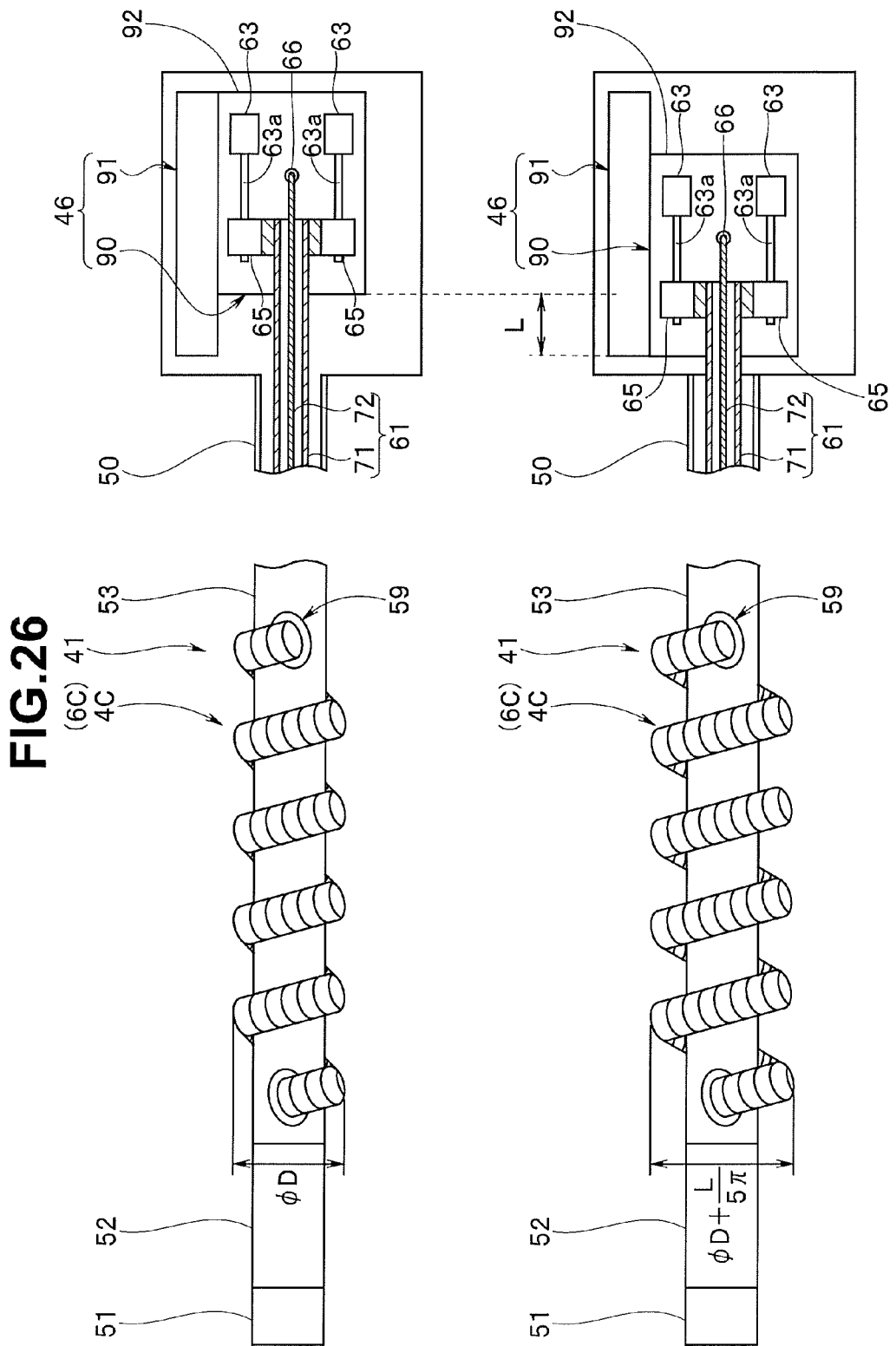

INTRADUCTAL INSERTION DEVICE

CROSS REFERENCE TO RELATED APPLICATION

This application is a continuation application of PCT/JP2010/063040 filed on Aug. 2, 2010 and claims benefit of Japanese Application No. 2009-207358 filed in Japan on Sep. 8, 2009, the entire contents of which are incorporated herein by this reference.

BACKGROUND OF THE INVENTION

1. Field of the Invention

The present invention relates to an intraductal insertion device which can advance and retract an insertion portion in a duct using thrust developed by a thrust generating section.

2. Description of the Related Art

Conventionally, an intraductal insertion device such as a catheter is inserted directly into the urethra or the like. Also, an elongated insertion portion of an endoscope is inserted, for example, into the stomach through the oral cavity, or into the large intestine or the like through the anus.

Generally, the endoscope is equipped with a bending portion on a distal end side of the elongated insertion portion, where the bending portion is configured by linking bending pieces together, for example, to perform bending operation in up-and-down and left-to-right directions. The bending portion is configured to perform bending operation when a surgeon operates, for example, a bending knob provided in an operation section and thereby advances and retracts an operation wire connected to the bending pieces.

It requires skill to learn to pass the insertion portion of the endoscope smoothly through an intricate duct in a short time. In particular, surgeons inexperienced in handling endoscopes used to take a lot of time inserting the insertion portion into deep part of the large intestine. Thus, in order to improve insertability of the insertion portion, various proposals have been made to pass the insertion portion through to a target site by means of thrust.

For example, U.S. Pat. No. 7,048,717 discloses an endoscope insertion aid device and the like equipped with a spiral structure. With the endoscope insertion aid device, when a spiral structural portion provided in an insertion portion of an endoscope is rotated around the axis of the insertion portion by rotating a handle, the spiral structural portion and large intestine walls form a relationship such as between an external thread and an internal thread, providing thrust for the insertion portion to move forward in the intestine.

On the other hand, Japanese Patent Application Laid-Open Publication No. 2006-523513 (hereinafter referred to as Patent Document 2) discloses a self-propelled endoscope apparatus used to transport ancillary devices to a desired location in a tubular space and environment in which medical and non-medical procedures are carried out. The self-propelled endoscope apparatus is made up of a flexible toroid filled with a fluid, and a frame equipped with a power unit or a frame supplied with power. A surface of the toroid of the endoscope apparatus circulates around the toroid by a continuous motion along a central axial line of the toroid, moving from inside a central cavity of the toroid to outside the toroid where the surface rotates in an opposite direction and returning again to the central cavity. The toroid is designed such that direction and speed of the toroid motion is controllable. Consequently, for example, when a colonoscope is inserted in a tubular space or environment such as the colon of a patient, the circulated toroid surface comes into contact with an inner surface of the tubular space, causing the endoscope apparatus to advance or retract.

SUMMARY OF THE INVENTION

An intraductal insertion device according to one aspect of the present invention comprises a thrust generating section installed at an insertion portion, wherein the thrust generating section includes a flexible shaft adapted to rotate clockwise or counterclockwise around a shaft axis; and the shaft axis of the flexible shaft is wound around an axis of the insertion portion in an insertion direction.

BRIEF DESCRIPTION OF THE DRAWINGS

FIG. 1 is a diagram illustrating an intraductal insertion device equipped with a thrust generating section arranged and configured by winding a flexible shaft around an outer circumferential face of a catheter body at least half a turn or more;

FIG. 2 is a sectional view illustrating a configuration on a distal end side of the flexible shaft wound around the outer circumferential face of the catheter body as well as how the flexible shaft is led out of an insertion portion;

FIG. 3 is a diagram when a shaft holding member is viewed from the side of a curved surface;

FIG. 4 is a diagram when the shaft holding member is viewed from a plane facing the curved surface; and FIG. 5 is a diagram illustrating operation of a catheter arranged by winding the flexible shaft around the outer circumferential face of the catheter body half a turn or more in a circumferential direction;

FIG. 6 is a sectional view illustrating a catheter body provided with a circumferential shaft groove; and FIG. 7 is a diagram illustrating operation of a catheter with the flexible shaft placed in the circumferential shaft groove of the catheter body.

FIGS. 8 to 10B are diagrams concerning a second embodiment of the present invention and illustrating a capsule endoscope equipped with a thrust generating section; where FIG. 9 is a longitudinal sectional view of the capsule endoscope equipped with the thrust generating section and is a diagram illustrating operation of the capsule endoscope;

FIG. 10B is a diagram illustrating a spirally-shaped portion when the circumferentially rotating capsule section is rotated one turn by the circumferentially rotating capsule section rotation motor;

FIG. 11 is a diagram illustrating a body insertion aid equipped with a thrust generating section;

FIG. 12 is a diagram when the body insertion aid is viewed in a direction of arrow 12Y in FIG. 11;

FIG. 13 is a sectional view illustrating a configuration of the flexible shaft; and FIG. 14 is a sectional view taken along line 14Y-14Y in FIG. 12 to illustrate operation of the body insertion aid;

FIG. 15 is a diagram illustrating an endoscope system equipped with an endoscope whose insertion portion is provided with a thrust generating section;

FIG. 16 is a diagram of the thrust generating section whose flexible shaft is covered with a spirally-shaped portion covering, as viewed in a direction of arrow 16Y in FIG. 15;

FIG. 17 is a diagram of the insertion portion covered with the spirally-shaped portion covering, as viewed in a direction of arrow 17Y in FIG. 16;

FIG. 18 is a diagram illustrating a configuration of the flexible shaft and an internal configuration of a rotational driving device;

FIG. 19 is a sectional view taken along line 19Y-19Y indicated by arrows in FIG. 16 to illustrate operation of the spirally-shaped portion and spirally-shaped portion covering, the spirally-shaped portion being made up of the flexible shaft provided in a flexible tube portion and the spirally-shaped portion covering being placed around the spirally-shaped portion;

FIG. 20 is a diagram illustrating a configuration of a shaft body;

FIG. 21 is a diagram illustrating operation of the insertion portion whose flexible portion is equipped with the thrust generating section made up of the flexible shaft covered with the spirally-shaped portion covering; and FIG. 22 is a diagram illustrating how the insertion portion has passed the splenic flexure by means of thrust developed by the thrust generating section provided in the flexible portion;

FIG. 26 is a diagram illustrating a configuration and operation of a rotational driving unit and a driving unit advance/retract device provided in the rotational driving device.

DETAILED DESCRIPTION OF THE PREFERRED EMBODIMENTS

Embodiments of the present invention will be described below with reference to the drawings.

A first embodiment of the present invention will be described with reference to FIGS. 1 to 5.

Figure 1:
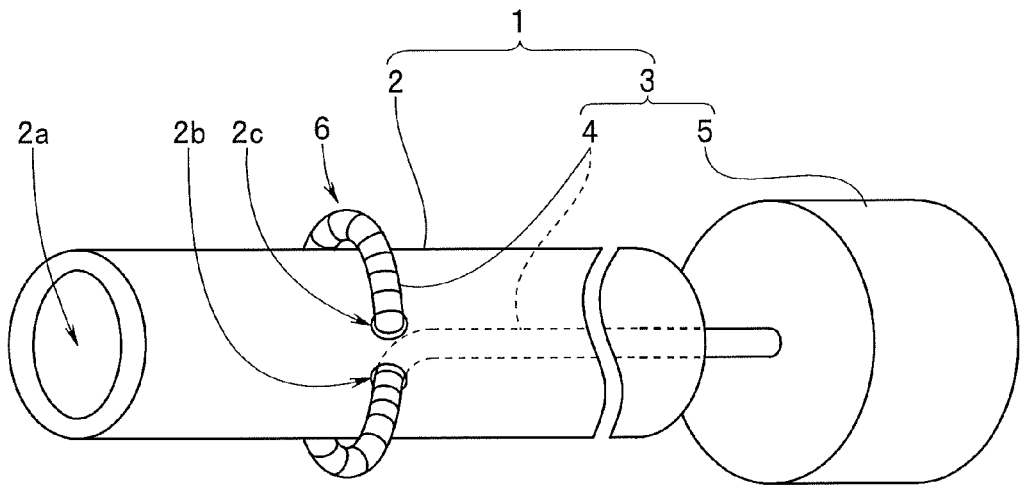
FIGS. 1 to 5 concern a first embodiment of the present invention, where.

A catheter 1 shown in FIG. 1 is an intraductal insertion device used, for example, to drain urine. The catheter 1 includes a catheter body 2 which is flexible and a thrust generating mechanism section 3. The catheter body 2 is an insertion portion inserted into a target site such as the urethra.

The thrust generating mechanism section 3 includes a flexible shaft 4 and an operation/grasping section 5. The flexible shaft 4, shaped in the form of a close-wound coil spring, is a rotating shaft which has flexibility and excels in rotation transmission. The operation/grasping section 5 is used to rotate the flexible shaft 4 clockwise or counterclockwise around a shaft axis. The operation/grasping section 5 is a cylindrical member made, for example, of resin and intended to be gripped by a surgeon. Incidentally, the shaft axis is a longitudinal central axis of the flexible shaft 4.

Figure 2:
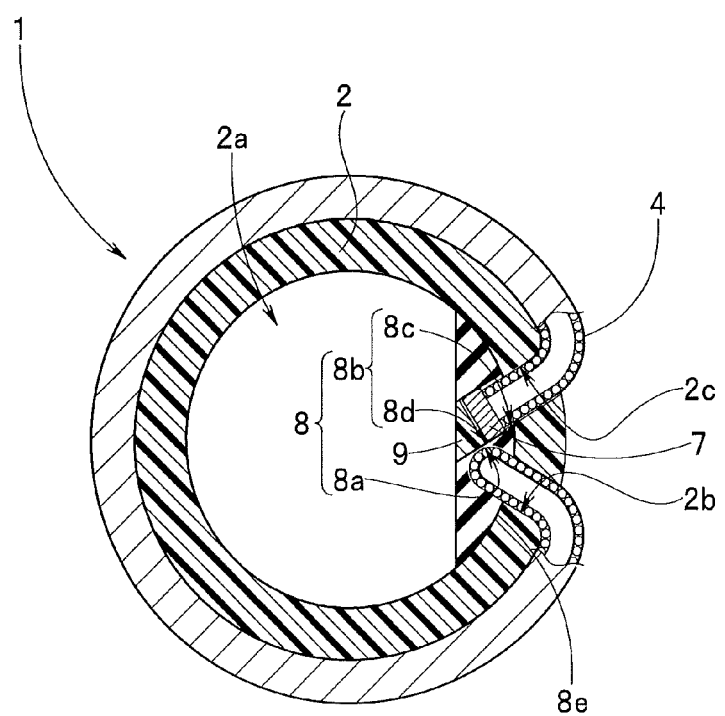

As shown in FIGS. 1 and 2, the catheter body 2 is an elongated tubular body and a through-hole 2a is formed through the catheter body 2, centering around a longitudinal axis. Also, a first hole 2b and a second hole 2c are formed in an outer circumferential face of the catheter body 2 to communicate between the through-hole 2a and the outside.

According to the present embodiment, the first hole 2b and the second hole 2c are formed such that respective centers will be located on the same circumference. The first hole 2b and the second hole 2c are provided so as to be spaced in a circumferential direction, for example, such that the flexible shaft 4 led out of the first hole 2b and led to the inside through the second hole 2c will be placed by being wound around the outer circumferential face of the catheter body 2 at least half a turn or more.

The flexible shaft 4 according to the present embodiment is mainly passed through the through-hole 2a of the catheter body 2. On a distal end side, the flexible shaft 4 is exposed from a distal end side portion of the outer circumferential face of the catheter body 2 and placed by being wound in the circumferential direction. A proximal end portion of the flexible shaft 4 is integrally fixed to the operation/grasping section 5. The distal end side of the flexible shaft 4 exposed from the distal end side portion of the outer circumferential face of the catheter body 2 is configured as a thrust generating section 6.

The distal end side of the flexible shaft 4 is led out of the through-hole 2a, for example, via the first hole 2b, subsequently placed on the side of the outer circumferential face where the first hole 2b and the second hole 2c are located at some distance from each other, and led into the through-hole 2a again through the second hole 2c. The distal end side of the flexible shaft 4 is designed to be placed in a predetermined portion of a shaft holding member 8 (described later) in such a way as to be turnable with respect to the second hole 2b.

Referring to FIG. 2, reference numeral 7 denotes a shaft distal end member. The shaft distal end member 7 is integrally fixed to a distal end of the flexible shaft 4 by joining such as soldering. The shaft distal end member 7 has, for example, a flat cylindrical shape, and outside diameter size of the shaft distal end member 7 is larger than diameter size of the flexible shaft 4. That is, the shaft distal end member 7 is a fall prevention member which prevents the distal end of the flexible shaft 4 from coming off a shaft passage hole 8c (described later).

Figure 3:
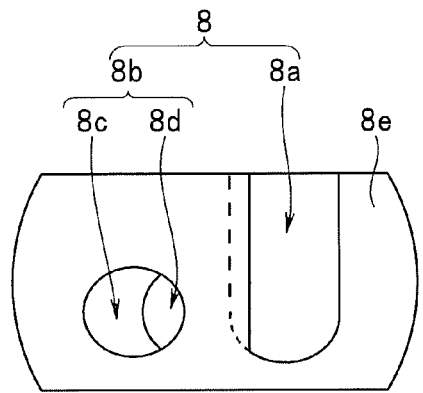
Figure 4:
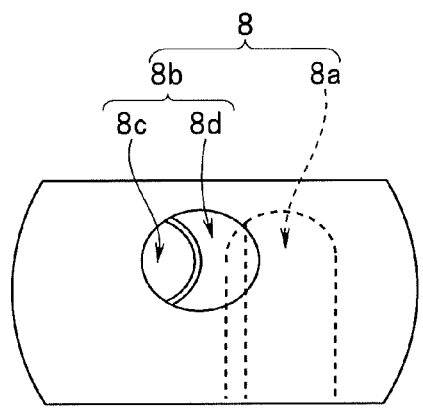

As shown in FIGS. 2 to 4, the shaft holding member 8 includes a shaft placement groove 8a and a shaft distal end holding hole 8b. The shaft placement groove 8a is formed into a curved shape so as to guide the flexible shaft 4 passing through the through-hole 2a to the first hole 2b.

The shaft distal end holding hole 8b is a stepped through-hole which has the shaft passage hole 8c and a shaft distal end placement hole 8d. The flexible shaft 4 is passed through the shaft passage hole 8c in a loosely fitted state. The shaft distal end member 7 is placed in the shaft distal end placement hole 8d in a loosely fitted state. That is, the shaft passage hole 8c is formed to be smaller in diameter size than the shaft distal end placement hole 8d.

Thus, the shaft distal end member 7 which makes up a distal end portion of the flexible shaft 4 is turnable in the shaft distal end placement hole 8d.

The shaft holding member 8 is made of flexible rubber or resin. The shaft holding member 8 is fixed integrally to a predetermined position of the through-hole 2a in the catheter body 2 by gluing or welding. Specifically, the shaft holding member 8 is integrally fixed to the catheter body 2, with a curved surface 8e of the shaft holding member 8 placed in close contact with an inner surface of the through-hole 2a, with the second hole 2c and the shaft distal end holding hole 8b communicated with each other, and with the first hole 2b facing the shaft placement groove 8a in a desired condition.

Incidentally, a plug member 9 may be disposed on an open side of the shaft distal end placement hole 8d. The plug member 9, when provided on the open side of the shaft distal end placement hole 8d, prevents the distal end portion of the flexible shaft 4, with the shaft distal end member 7 fixedly mounted thereon, form falling off the shaft distal end placement hole 8d to inside the through-hole 2a.

Operation of the catheter 1 configured as described above will be described.

When inserting the catheter body 2 of the catheter 1 into the urethra 10, the surgeon inserts the catheter body 2 gradually into the urethra 10 by gripping the catheter body 2 with one hand and gripping the operation/grasping section 5 with the other hand. Then, with the flexible shaft 4 of the catheter body 2 placed in contact with a wall 10a of the urethra 10, the surgeon performs a rotation operation on the operation/grasping section 5.

Figure 5:
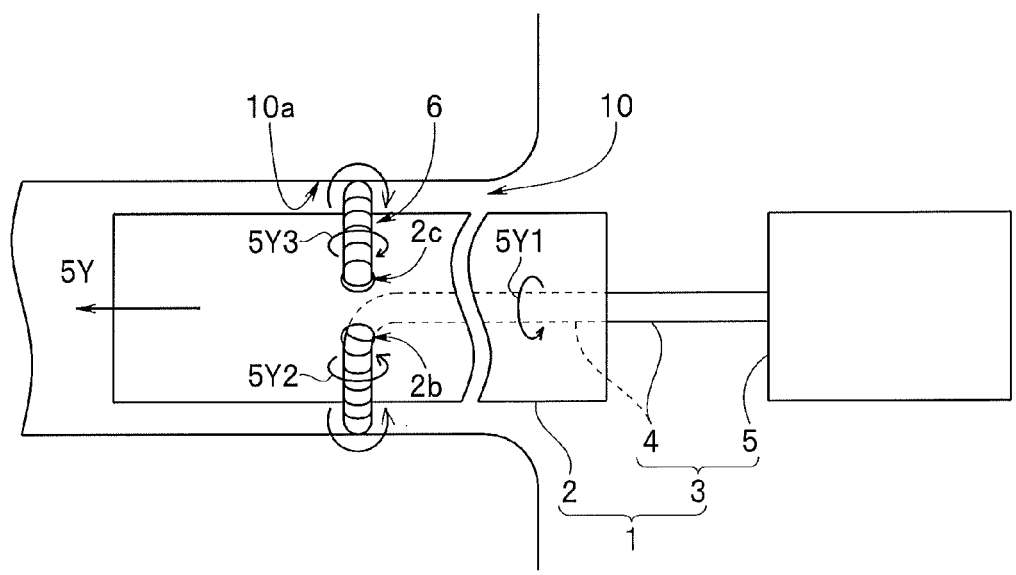

Consequently, as shown in FIG. 5, the flexible shaft 4 rotates in the through-hole 2a as indicated by arrow 5Y1. Then, a rotational force resulting from the rotation operation of the operation/grasping section 5 is gradually transmitted to the distal end side. Consequently, the flexible shaft 4 placed on a distal end side of the outer circumferential face of the catheter body 2 rotates as indicated by arrows 5Y2 and 5Y3. Subsequently, the shaft distal end member 7 placed in the shaft distal end placement hole 8d also enters a rotating state, resulting in rotation of the entire flexible shaft 4. Then, as the surgeon continues the rotation operation of the operation/grasping section 5, the flexible shaft 4 continues to rotate.

In so doing, that part of the flexible shaft 4 which is located on an undersurface of the catheter body 2 in the FIG. 5 rotates counterclockwise around an axis perpendicular to the plane of the paper and that part of the flexible shaft 4 which is located on a top surface rotates clockwise around the axis perpendicular to the plane of the paper. That is, since the flexible shaft 4 is placed in the circumferential direction on the distal end side of the outer circumferential face of the catheter body 2, the axial rotation of the flexible shaft 4 passing through the through-hole 2a, on the outer circumferential face, is rotation around an axis orthogonal to an insertion direction. In other words, the flexible shaft 4 is wound such that the shaft axis of the flexible shaft 4 will be orthogonal to the insertion direction on the outer circumferential face of the catheter body 2.

Consequently, since the flexible shaft 4 being rotated remains in contact with the wall 10a, a frictional force is generated between the wall 10a and the flexible shaft 4 and acts as thrust which moves the catheter body 2 in a direction of arrow 5Y. This allows the surgeon to push the catheter body 2 forward smoothly into deep part using, as auxiliary power, the thrust developed by the rotating flexible shaft 4 placed in contact with the wall 10a.

In this way, the flexible shaft 4 is axially rotated through rotation operation of the operation/grasping section 5. In the rotating state, since the flexible shaft 4 wound in the circumferential direction around the outer circumferential face of the catheter body 2 on the distal end side is placed in contact with the wall, the flexible shaft 4 provides thrust used to advance or retract the catheter body 2.

This makes it possible to insert the catheter body 2 smoothly into the urethra 10.

Also, by simply placing part of the flexible shaft 4 on the outer circumferential face of the catheter body 2, it is possible to reduce the diameter of the catheter equipped with the thrust generating section 6.

Incidentally, if the operation/grasping section 5 is rotated in such a way as to rotate the flexible shaft 4 in the through-hole 2a in a direction opposite to arrow 5Y1, the flexible shaft 4 placed in contact with the wall 10a provides thrust which tends to move the catheter body 2 in a direction opposite to the direction of arrow 5Y, i.e., retract the catheter body 2.

A variation of the catheter will be described with reference to FIGS. 6 and 7.

Figure 6:
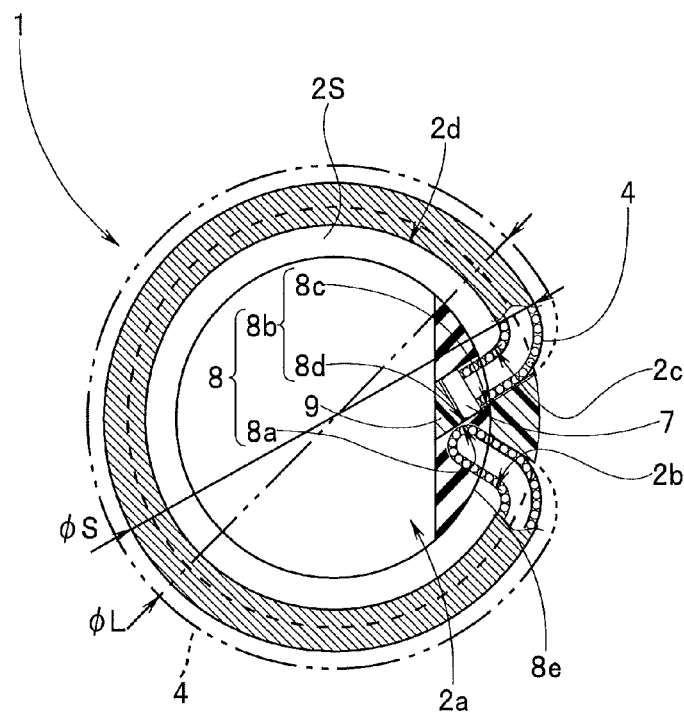
FIGS. 6 and 7 concern a variation of the first embodiment, where.
Figure 7:
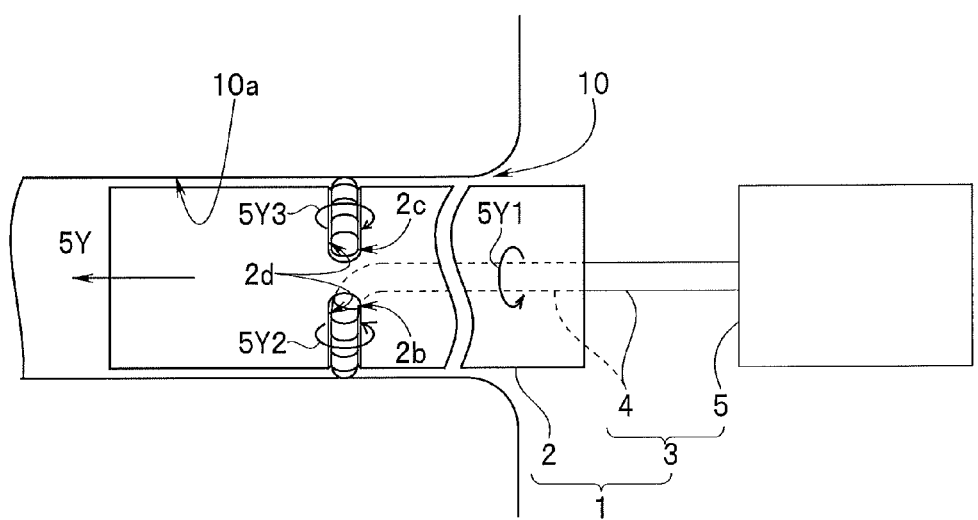

As shown in FIGS. 6 and 7, a catheter body 2S has a circumferential shaft groove 2d of a predetermined depth formed in an outer circumferential face of the catheter body 2 extending from the first hole 2b to the second hole 2c. The flexible shaft 4 is placed in the circumferential shaft groove 2d.

Consequently, maximum outside diameter $\phi S$ of the insertion portion of the catheter body 2 with the flexible shaft 4 placed in the circumferential shaft groove 2d as shown in FIG. 6 can be made smaller than maximum outside diameter $\phi L$ (indicated by a chain double-dashed line) of the insertion portion of the flexible shaft 4 placed along the outer circumferential face 2o of the catheter body 2 as in the case of the embodiment described above.

Also, the flexible shaft 4, when placed in the circumferential shaft groove 2d, can prevent a placement location of the flexible shaft 4 from being changed by resistance from the wall 10a when the catheter body 2 is inserted into the urethra 10. Consequently, the flexible shaft 4 comes into contact with the wall 10a in a stable manner, readily providing thrust used to advance the catheter body 2.

Desirably, the depth of the circumferential shaft groove 2d is not larger than half the diameter of the flexible shaft 4, and approximately half the circumference of the flexible shaft 4 is placed in the circumferential shaft groove 2d.

Also, in the embodiment described above, the thrust generating section is configured by forming the first hole 2b and the second hole 2c on the same circumference and placing the flexible shaft 4 in the circumferential direction on the distal end side of the outer circumferential face of the catheter body 2. However, with the first hole 2b and the second hole 2c formed so as to be spaced in a longitudinal direction of the catheter body 2, the flexible shaft 4 led out through the first hole 2b may be wound around the outer circumferential face of the catheter body 2, forming a spiral shape, which can be used as a thrust generating section.

Furthermore, in the embodiment described above, the surgeon performs a rotation operation manually by gripping the operation/grasping section 5. However, a driving device adapted to rotate the operation/grasping section 5 may be provided to axially rotate the flexible shaft 4.

Besides, in the embodiment described above, the intraductal insertion device is a catheter used to drain urine. However, the catheter is not limited to a urethral catheter, and the thrust generating section 6 may be provided on catheters for other lumens such as digestive tracts, the trachea, and blood vessels.

A second embodiment of the present invention will be described with reference to FIGS. 8 to 10B.

Figure 8:
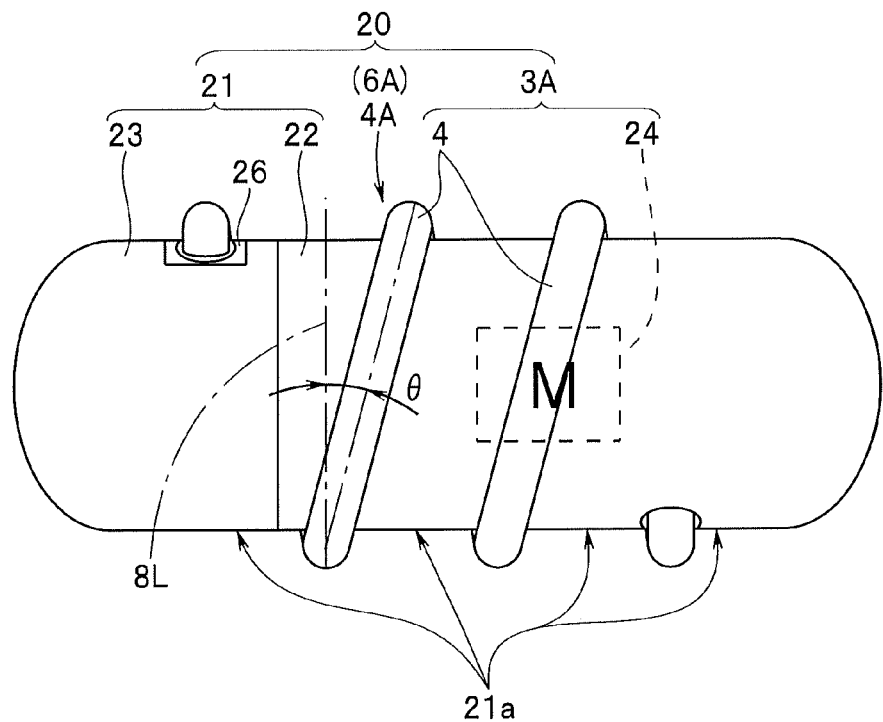

FIG. 8 shows a capsule endoscope 20, which is configured by providing a thrust generating mechanism section 3A on a capsule 21 whose opposite end portions are hemispherical. The capsule endoscope 20 includes an observation optical system, an illumination optical system, various circuits, and the like, which are not shown in the capsule 21 and description of which will be omitted in the present embodiment.

The capsule 21, which is an insertion portion swallowed and inserted into a lumen, includes a capsule body 22 and a circumferentially rotating capsule section 23. The circumferentially rotating capsule section 23 is mounted on an open side of the capsule body 22 in such a way as to rotate clockwise and counterclockwise.

The thrust generating mechanism section 3A includes a flexible shaft 4 and a shaft rotation motor 24 which is a drive motor. The flexible shaft 4 is provided as a bendable spirally-shaped portion 4A wound a predetermined number of turns around an outer circumferential face of a trunk portion 21a of the capsule 21, where the trunk portion 21a has a fixed outside diameter size. According to the present embodiment, the spirally-shaped portion 4A is a thrust generating section 6A configured by winding the flexible shaft 4 from right to left, where the number of turns is 2.5 turns. Incidentally, winding from right to left means winding counterclockwise from the surgeon's hand side toward the distal end when viewed in the travel direction of the capsule body from the surgeon's hand side. On the other hand, winding from left to right (described later) means winding clockwise from the surgeon's hand side toward the distal end.

Figure 9:
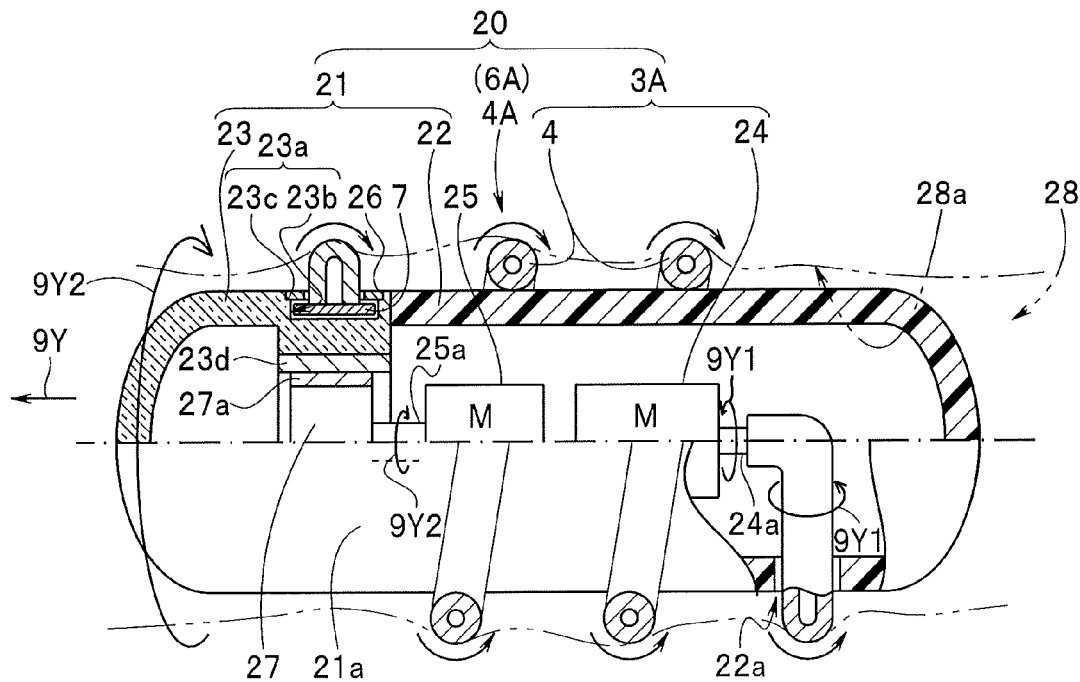

As shown in FIG. 9, a shaft distal end member 7 is fixedly mounted on one end of the flexible shaft 4 which makes up the spirally-shaped portion 4A. A stepped hole 23a is formed in the circumferentially rotating capsule section 23 in order for the shaft distal end member 7 to be loosely fitted therein. The shaft distal end member 7 is placed in a recessed portion 23b. An opening of the recessed portion 23b is plugged by fixing a lid member 26 to a stepped portion 23c, for example, by gluing, with the shaft distal end member 7 placed in the recessed portion 23b. This allows that end portion of the flexible shaft 4 to which the shaft distal end member 7 is attached to be turnably mounted on the circumferentially rotating capsule section 23.

The proximal end portion of the flexible shaft 4 has been introduced into an inner space of the capsule 21 through a body-side hole 22a formed in the capsule body 22. A shaft rotation motor (hereinafter simply referred to as a first motor) 24 and a circumferentially rotating capsule section rotation motor (hereinafter simply referred to as a second motor) 25 are fixed to a predetermined location of the capsule body 22.

The other end of the flexible shaft 4 introduced into the inner space of the capsule 21 is fixed to a first motor shaft 24a of the first motor 24. Consequently, when the first motor shaft 24a is rotated, for example, in a direction of arrow 9Y1 by driving the first motor 24, the flexible shaft 4 starts to rotate axially in the inner space.

The rotation of the flexible shaft 4 transmitted gradually to the distal end side is transmitted via the flexible shaft 4 wound around the trunk portion 21a and thereby puts the shaft distal end member 7 placed in the recessed portion 23b into a rotating state. Then, the rotation of the flexible shaft 4 continues. In so doing, that part of the flexible shaft 4 which is located on an undersurface of the trunk portion 21a in FIG. 9 rotates counterclockwise around an axis perpendicular to the plane of the paper. On the other hand, that part of the flexible shaft 4 which is located on a top surface of the trunk portion 21a in FIG. 9 rotates clockwise around the axis perpendicular to the plane of the paper.

As described above, the flexible shaft 4 makes up the spirally-shaped portion 4A by spiraling around the trunk portion 21a. A rotation axis of the flexible shaft 4 is positioned so as to be substantially orthogonal to an insertion direction of the capsule 21. Therefore, the axial rotation of the flexible shaft 4 in the inner space of the capsule 21 is performed around the rotation axis substantially orthogonal to the insertion direction on the outer circumferential face of the trunk portion 21a. In other words, the flexible shaft 4 is wound in such a way that the shaft axis of the flexible shaft 4 will be substantially orthogonal to the insertion direction on the outer circumferential face of the trunk portion 21a of the capsule 21.

The state of being substantially orthogonal here allows for an angle of θ between an imaginary line (denoted by reference numeral 8L in FIG. 8) orthogonal to a longitudinal axis of the capsule 21 and the inclined central axis of the spiraling flexible shaft 4 (both inclusive).

Consequently, as the flexible shaft 4 is placed in contact with a wall 28a of a lumen 28, thrust is generated, allowing the capsule 21 to advance deep into the lumen 28 in a direction of arrow 9Y.

Incidentally, if the first motor shaft 24a is rotated, for example, in a direction opposite to the direction of arrow 9Y1 by driving the first motor 24, that part of the flexible shaft 4 which is located on the undersurface of the trunk portion 21a in FIG. 9 rotates clockwise around an axis perpendicular to the plane of the paper and that part of the flexible shaft 4 which is located on the top surface in FIG. 9 rotates counterclockwise around the axis perpendicular to the plane of the paper.

The second motor 25 is fixedly mounted on the capsule body 22 such that a second motor shaft 25a of the second motor 25 will coincide with the longitudinal axis of the capsule 21. A gear 27 with a predetermined tooth portion 27a on an outer circumferential face is fixedly mounted on the second motor shaft 25a of the second motor 25. The tooth portion 27a of the gear 27 meshes with an inner tooth portion 23d formed in a predetermined location of an inner circumferential face of the circumferentially rotating capsule section 23.

Therefore, if the second motor shaft 25a is rotated, for example, in a direction of arrow 9Y2 by driving the second motor 25, the gear 27 rotates in the same direction. Then, along with the rotation of the gear 27, the circumferentially rotating capsule section 23, in which the inner tooth portion 23d meshed with the tooth portion 27a of the gear 27 is formed, also rotates in the direction of arrow 9Y2.

Figure 10A:
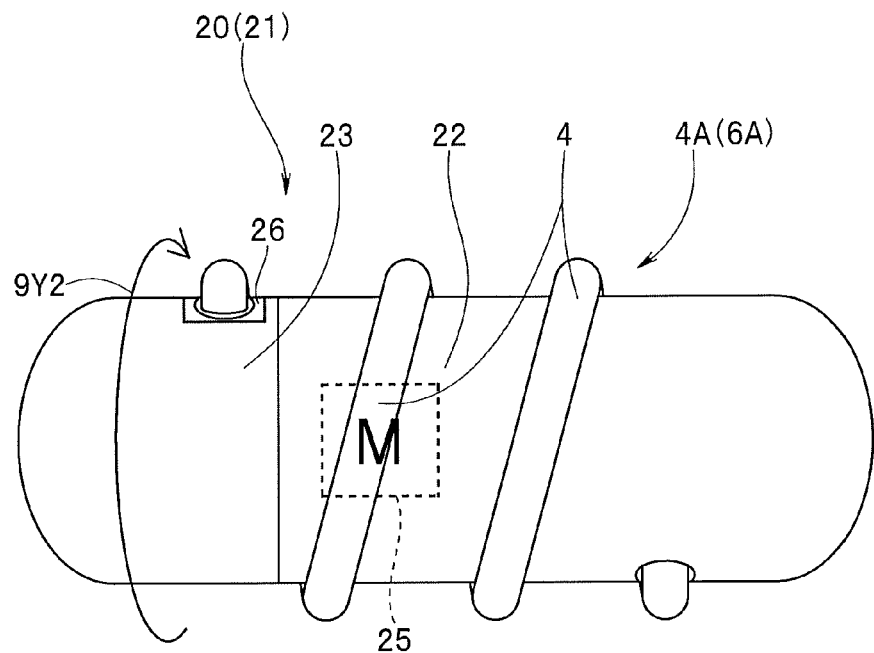
FIG. 10A is a diagram illustrating a relationship between a circumferentially rotating capsule section rotation motor and a circumferentially rotating capsule section.

As shown in FIG. 10A, when the circumferentially rotating capsule section 23 rotates in the direction of arrow 9Y2 under the driving force of the second motor 25, the distal end portion of the flexible shaft 4 equipped with the shaft distal end member 7 changes its position along with the rotation, gradually unwinding the spirally-shaped portion 4A.

Consequently, the flexible shaft 4 wound tight around the outer circumferential face of the trunk portion 21a is separated gradually from the outer circumferential face, causing increases in outside diameter size of the spirally-shaped portion 4A.

Figure 10B:
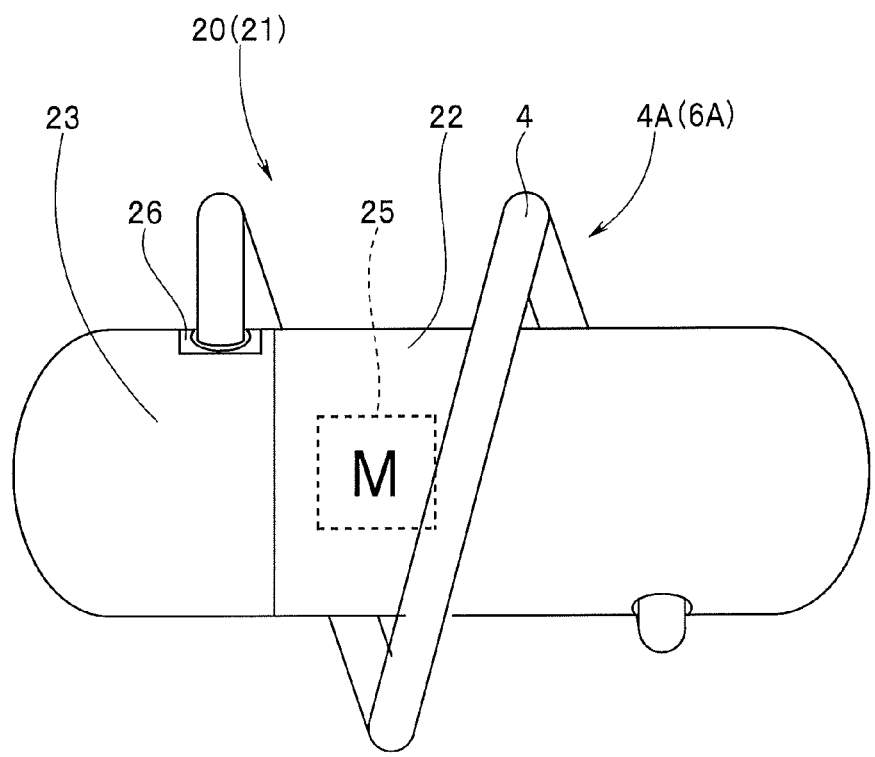

When the circumferentially rotating capsule section 23 rotates one turn in the direction of arrow 9Y2, the number of turns of the spirally-shaped portion 4A formed around the trunk portion 21a changes from 2.5 turns to 1.5 turns as shown in FIG. 10B. Consequently, the spirally-shaped portion 4A increases in outside diameter size by an amount corresponding to one turn.

Operation of the capsule endoscope 20 configured as described above will be described.

Upon determining that the capsule endoscope 20 swallowed by the patient has passed, for example, the stomach, the surgeon turns on the first motor 24 and rotates the first motor shaft 24a in the direction of arrow 9Y1 in FIG. 9. Consequently, the flexible shaft 4 making up the spirally-shaped portion 4A rotates as follows: the part located on the undersurface of the trunk portion 21a in FIG. 9 rotates counterclockwise around an axis perpendicular to the plane of the paper as described above and the part located on the top surface rotates clockwise around the axis perpendicular to the plane of the paper.

In the rotating state, since the spirally-shaped portion 4A is placed in contact with the wall 28a of the lumen 28 as shown in FIG. 9, a frictional force is generated between the wall 28a and the flexible shaft 4 and acts as thrust which advances the capsule 21 deep into the lumen 28 in the direction of arrow 9Y. During an examination, if the surgeon wants to advance the capsule 21 in a direction opposite to the direction of arrow 9Y, the surgeon rotates the first motor shaft 24a of the first motor 24 in the direction opposite to the direction of arrow 9Y1.

On the other hand, if the surgeon determines that the capsule 21 is advancing without obtaining thrust during the examination, the surgeon gradually rotates the second motor shaft 25a of the second motor 25 in the direction of arrow 9Y2 to bring the spirally-shaped portion 4A into contact with the wall 28a of the lumen 28. Consequently, the spirally-shaped portion 4A gradually increases in outside diameter. Then, if it is determined that the spirally-shaped portion 4A increasing in outside diameter is in contact with the wall 28a of the lumen 28, causing the capsule 21 to move under thrust, the surgeon maintains the outside diameter size of the spirally-shaped portion 4A. Consequently, the capsule 21 moves under the thrust.

In this way, in the capsule endoscope 20, the trunk portion 21a of the capsule 21 is provided with the spirally-shaped portion 4A formed by spirally winding the flexible shaft 4. The flexible shaft 4 formed into the spirally-shaped portion 4A increases an area of contact with an inner wall of the lumen, making thrust readily available.

Also, the second motor 25 is provided in the capsule 21 to turn the circumferentially rotating capsule section 23 with respect to the capsule body 22. Besides, one end of the flexible shaft 4 which forms the spirally-shaped portion 4A is fixed to the circumferentially rotating capsule section 23 while the other end is fixed to the first motor shaft 24a of the first motor 24 in the capsule body 22 via the body-side hole 22a of the capsule body 22. This makes it possible to adjust the outside diameter size of the spirally-shaped portion 4A so as to come into contact with the entire circumference of the intestine by driving the second motor 25 as required and thereby allows thrust to be obtained efficiently.

Therefore, even if there is a difference between the inside diameter of the lumen and the outside diameter of the capsule endoscope 20 due to individual differences or observed sites, observations can be carried out properly by adjusting the outside diameter of the spirally-shaped portion 4A of the capsule endoscope 20 to the inside diameter of the lumen.

The rest of the operation and other advantages are the same as those of the embodiment described above.

Incidentally, according to the present embodiment, the spirally-shaped portion 4A of the capsule endoscope 20 is wound from right to left. However, the spirally-shaped portion 4A is not limited to winding from right to left, and may be wound from left to right. In that case, rotating the first motor shaft 24a of the first motor 24 in the direction opposite to the direction of arrow 9Y1 provides thrust used to advance the capsule 21 deep into the lumen 28 in the direction of arrow 9Y. Also, the number of turns of the spirally-shaped portion 4A is not limited to 2.5 turns, and may be larger or smaller.

A third embodiment of the present invention will be described with reference to FIGS. 11 to 14.

Figure 11:
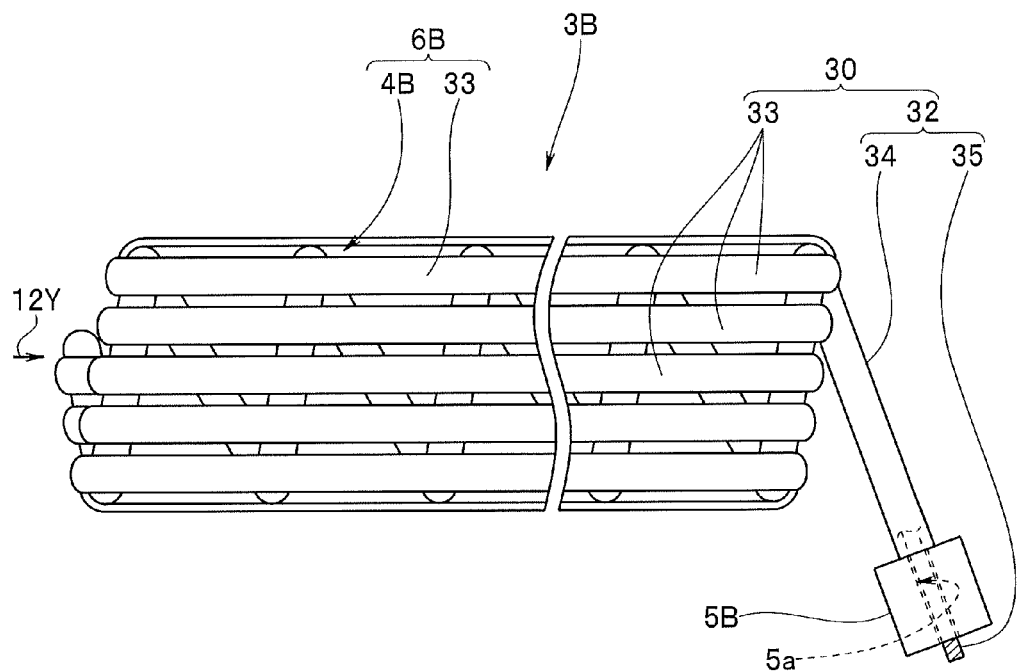
FIGS. 11 to 14 concern a third embodiment of the present invention, where.
Figure 12:
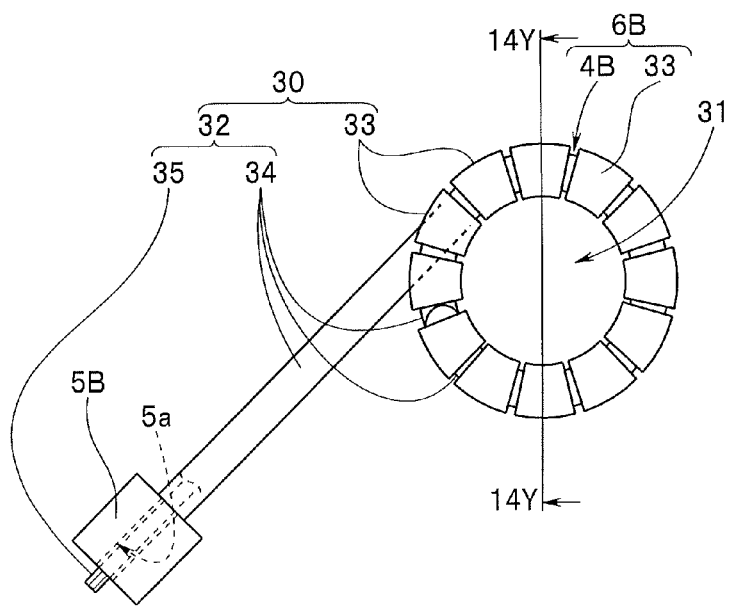

FIGS. 11 and 12 show a body insertion aid 30 equipped with a thrust generating mechanism section 3B. The body insertion aid 30 is used in combination with, for example, a catheter for digestive tracts, the trachea, blood vessels, or the urethra or a medical instrument such as an endoscope for the stomach, the small intestine, or the large intestine. Specifically, the body insertion aid 30 includes a longitudinal hollow portion 31 through which a catheter or the insertion portion of an endoscope is passed.

The thrust generating mechanism section 3B of the body insertion aid 30 includes a flexible shaft 32, multiple ring-shaped belts 33, and an operation/grasping section 5B.

The flexible shaft 32 mainly makes up a spirally-shaped portion 4B equipped with the longitudinal hollow portion 31. The spirally-shaped portion 4B is configured, for example, by winding the flexible shaft 32 from right to left. The spirally-shaped portion 4B is an insertion portion inserted near a target site. The length of the spirally-shaped portion 4B is set approximately equal to the length of the catheter or the length of the insertion portion of an endoscope.

A proximal end side of the flexible shaft 32 is extended outward from the longitudinal hollow portion 31 of the spirally-shaped portion 4B as shown in FIG. 12. This prevents the flexible shaft 32 from crossing a proximal end opening of the longitudinal hollow portion 31, blocking the proximal end opening, and making it difficult to insert the catheter body or the insertion portion of the endoscope through the proximal end opening. A proximal end of the flexible shaft 32 is fixed to the operation/grasping section 5B gripped by the surgeon.

According to the present embodiment, a thrust generating section 6B is configured to be bendable using the spirally-shaped portion 4B and the multiple ring-shaped belts 33. Each of the ring-shaped belt 33 is placed by being wound around the spirally-shaped portion 4B. The ring-shaped belt 33 is a covering member with which the spirally-shaped portion 4B is covered. The ring-shaped belt 33 is a belt strip made of rubber or resin and having predetermined elasticity and predetermined length.

Each belt strip covers an inner surface of the spirally-shaped portion 4B, for example, starting from the distal end to the proximal end, and then after being turned to the side of an outer surface, covers the outer surface, starting from the proximal end to the distal end. Then, end faces of the belt are joined together by gluing or welding, and consequently the belt strip is wound around the spirally-shaped portion 4B as the ring-shaped belt 33. An outer circumference of the spirally-shaped portion 4B is covered by the multiple ring-shaped belts 33.

Figure 13:
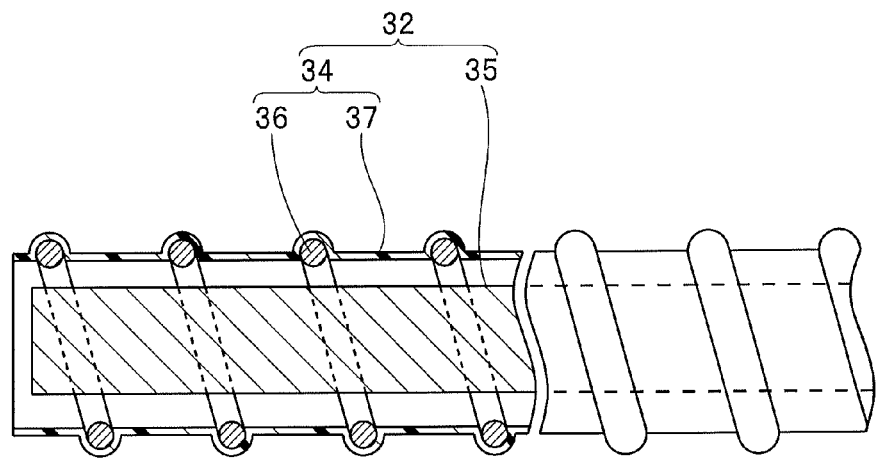

As shown in FIGS. 11 to 13, the flexible shaft 32 according to the present embodiment includes a spirally-shaped tube 34 which is a sheath body and a core wire 35 which is a central body. The core wire 35 is passed through the spirally-shaped tube 34 in a loosely fitted state. The core wire 35 is made, for example, of an aluminum alloy. The core wire 35 is capable of holding the spiral shape of the spirally-shaped portion 4B encircled with the ring-shaped belts 33 and is configured to be elastically deformable under external forces.

The spirally-shaped tube 34 has flexibility. The spirally-shaped tube 34 is integrally made up of a sparsely wound metal coil 36 and a resin coating 37 covering the metal coil 36. The metal coil 36 is made, for example, of a nickel-titanium alloy while the resin coating 37 is made of a urethane resin.

Incidentally, the metal coil 36 is not limited to nickel-titanium alloys, and may be made of another metal or made of resin. Also, the resin coating 37 is not limited to urethane resins, and may be made, for example, of a thermoplastic resin, polyester, or the like.

As shown in FIG. 12, the proximal end of the spirally-shaped tube 34 which makes up the flexible shaft 32 extended outward from the proximal end opening of the spirally-shaped portion 4B is integrally fixed to the operation/grasping section 5B. On the other hand, the core wire 35 of the flexible shaft 32 is configured to be able to be extended outward from an end face of the operation/grasping section 5B through a through-hole 5a formed in the operation/grasping section 5B.

Operation of the body insertion aid 30 configured as described above will be described.

The body insertion aid 30 has the longitudinal hollow portion 31 which allows passage of a urethral catheter. To insert the body insertion aid 30 into the urethra 10, the surgeon inserts the spirally-shaped portion 4B into the urethra 10 by gripping the spirally-shaped portion 4B encircled with the ring-shaped belts 33 with one hand and gripping the operation/grasping section 5B with the other hand. When a distal end side of the spirally-shaped portion 4B is inserted a desired amount into the urethra 10, the surgeon performs a rotation operation of the operation/grasping section 5B.

Figure 14:
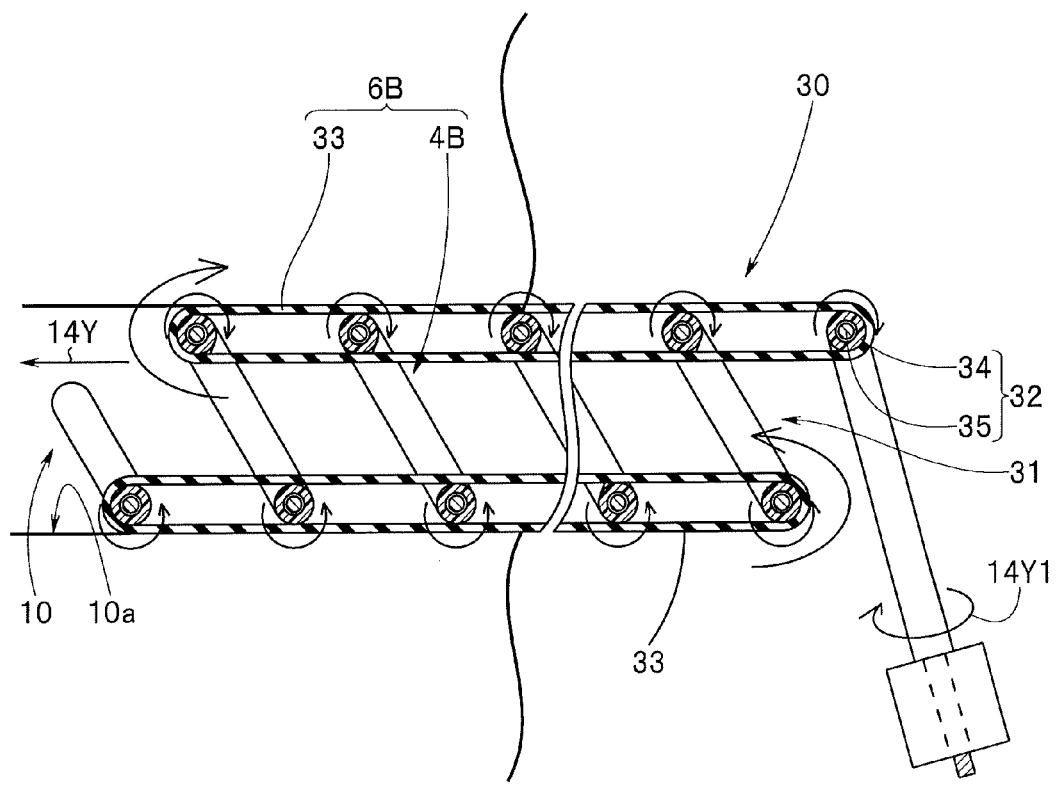

Consequently, as shown in FIG. 14, the spirally-shaped tube 34 of the flexible shaft 32 rotates as indicated by arrow 14Y1. That is, that part of the spirally-shaped tube 34 which makes up an upper side of the spirally-shaped portion 4B in FIG. 14 rotates clockwise around an axis perpendicular to the plane of the paper and that part of the spirally-shaped tube 34 which makes up a lower side rotates counterclockwise around the axis perpendicular to the plane of the paper.

Since inner surfaces of the ring-shaped belts 33 abut the spirally-shaped tube 34, the ring-shaped belts 33 rotate along with rotation of the spirally-shaped tube 34 in the same direction. In so doing, as outer surfaces of the ring-shaped belts 33 are placed in contact with the wall 10a of the urethra 10, a frictional force is generated between the ring-shaped belts 33 and the wall 10a. The frictional force provides the thrust used to move the body insertion aid 30 in a direction of arrow 14Y. This allows the surgeon to push the body insertion aid 30 forward smoothly into deep part using, as auxiliary power, the thrust provided by the ring-shaped belts 33.

After confirming that a distal end portion of the body insertion aid 30 has reached near the bladder, the surgeon leads a distal end of the urethral catheter to the bladder through the longitudinal hollow portion 31 of the body insertion aid 30.

In this way, in the body insertion aid 30, the thrust generating section 6B is configured by winding the multiple ring-shaped belts 33 around the spirally-shaped portion 4B with the multiple ring-shaped belts 33 kept in contact with the spirally-shaped portion 4B. Consequently, by turning the spirally-shaped tube 34 of the flexible shaft 32 of the spirally-shaped portion 4B, the ring-shaped belts 33 wound around the spirally-shaped portion 4B can be rotated clockwise or counterclockwise. Besides, as the ring-shaped belts 33 wound around the spirally-shaped portion 4B are placed in contact with the wall 10a, rotation of the ring-shaped belts 33 provides the thrust used to advance or retract the body insertion aid 30.

Also, the thrust generating section 6B made up of the spirally-shaped portion 4B and the multiple ring-shaped belts 33 placed by being wound around the spirally-shaped portion 4B is configured to be bendable. This allows the body insertion aid 30 to be inserted into a curved duct.

Also, with the body insertion aid 30, the ring-shaped belts 33 wound around the spirally-shaped portion 4B are placed in contact with the wall. This increases a contact area between the thrust generating section 6B and the wall compared to when the flexible shaft 4 is placed in contact with the wall such as in the embodiment described above, and thereby makes thrust readily available.

Incidentally, the spirally-shaped portion 4B may be used singly as the thrust generating section without being covered by the multiple ring-shaped belts 33. This eliminates the need for the power used to rotate the ring-shaped belts 33.

The rest of the operation and other advantages are the same as those of the embodiments described above.

A fourth embodiment of the present invention will be described with reference to FIGS. 15 to 22.

Figure 15:
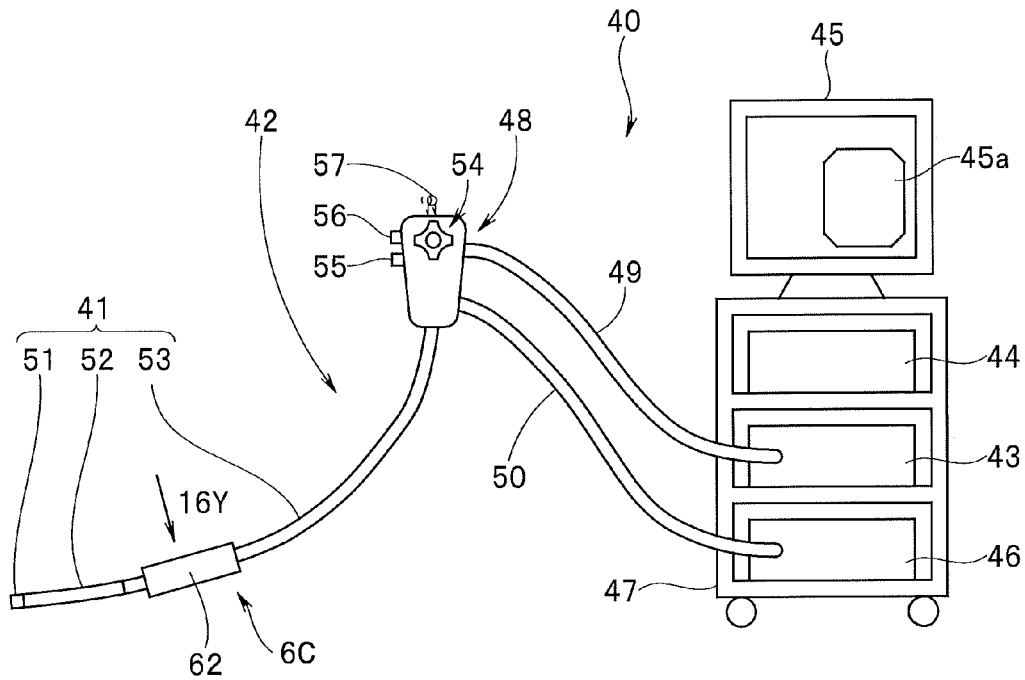
FIGS. 15 to 22 concern a fourth variation of the present invention, where.

In FIG. 15, reference numeral 40 denotes an endoscope system. The endoscope system 40 includes an endoscope 42, a light source device 43, a video processor 44, a monitor 45, and a rotational driving device 46, where the endoscope 42 includes a thrust generating mechanism section 3C in an insertion portion 41 and the rotational driving device 46 is a driving section for the thrust generating mechanism section 3C. Reference numeral 47 denotes a trolley on which the light source device 43, the video processor 44, the monitor 45, and the rotational driving device 46 are mounted.

The insertion portion 41 has flexibility and elongated shape in order to be inserted into a lumen. An operation section 48 is provided in a proximal end portion of the insertion portion 41. A universal code 49 and a rotational driving force transmission tube 50 extend outward from lateral part of the operation section 48. A proximal end portion of the universal code 49 is connected to the light source device 43. A proximal end portion of the rotational driving force transmission tube 50 is connected to the rotational driving device 46.

The light source device 43 supplies the endoscope 42, for example, with illumination light for normal light observation mode, i.e., white light radiated for observation of a site to be treated, and illumination light for narrow-band observation mode, i.e., narrow-band light emitted for detection of cancer and the like. The illumination light is emitted from an illumination window (reference numeral 51a in FIG. 16) of the illumination optical system.

The video processor 44 is provided with a drive circuit (not shown), a signal processing circuit (not shown), and the like. The drive circuit drives an image pickup device (not shown) of the endoscope 42. The signal processing circuit receives an electrical signal resulting from photoelectric conversion of an image formed on an image pickup surface of the image pickup device through an observation window (reference numeral 51b in FIG. 16) of the observation optical system and converts the electrical signal into a video signal. The video signal generated by the signal processing circuit is outputted to a monitor 45, and consequently the image captured by the image pickup device is displayed on a display screen 45a of the monitor 45.

The insertion portion 41 includes a distal end portion 51, a bending portion 52, and a flexible tubular portion 53 which are linked in the order starting from the distal end side. The bending portion 52 is configured to bend in up-and-down and left-to-right directions, for example, by linking multiple bending pieces together. The flexible tubular portion 53 is provided with the thrust generating mechanism section 3C.

The operation section 48 is provided, for example, with a bending operation knob 54, an air/water supply button 55, a suction button 56, a rotational driving device operation switch (hereinafter simply referred to as an operation switch) 57, and the like. The operation switch 57 turns on the rotational driving device 46.

The bending operation knob 54 causes the bending portion 52 to perform bending actions. When operated by the surgeon, the bending operation knob 54 causes the bending portion 52 to bend by drawing and relaxing a bending wire extending outward from the bending portion 52. The air/water supply button 55 is used to control air/water supply. The air/water supply button 55 is an operation button used to spray air or water toward the observation window 51*b* and the like from a nozzle (reference numeral 51*c* in FIG. 16). Either air or water is supplied depending on the operation performed by the surgeon. The suction button 56 is used to control suction. The suction button 56 is operated by the surgeon to suck body fluids, the water sprayed to the observation window, and the like through a distal end opening (reference numeral 51*d* in FIG. 16) provided in the distal end portion 51.

The thrust generating mechanism section 3C will be described with reference to FIGS. 16 to 20.

Figure 18:
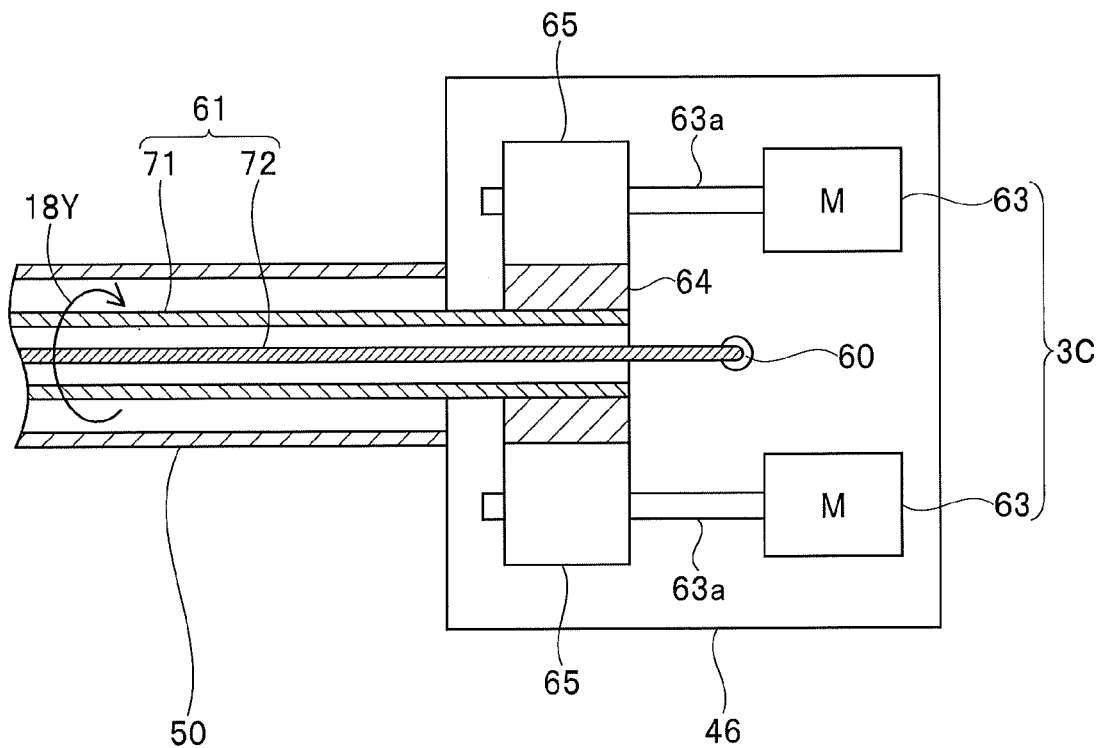

The thrust generating mechanism section 3C includes a flexible shaft 61 and a spirally-shaped portion covering (hereinafter simply referred to as a covering) 62 shown in FIG. 16 as well as a pair of rotation motors 63 provided in the rotational driving device 46 and shown in FIG. 18. A driving force transmission gear 64 is fixed to a proximal end portion of the flexible shaft 61. The driving force transmission gear 64 meshes with gears 65 fixedly mounted, respectively, on motor shafts 63*a* of the pair of rotation motors 63. The driving force transmission gear 64 is sandwiched between the pair of gears 65.

The flexible shaft 61 is configured to rotate in a direction of arrow 18Y or in the opposite direction by being driven by the pair of rotation motors 63.

Figure 16:
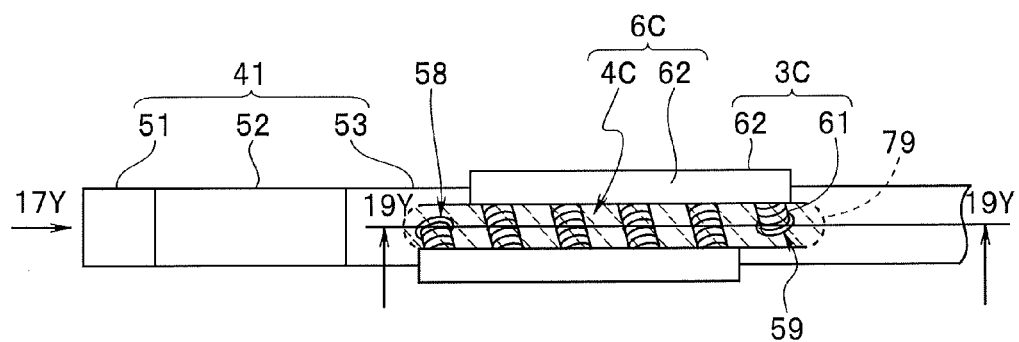

As shown in FIG. 16, on the distal end side, the flexible shaft 61 is formed into a spirally-shaped portion 4C wound from left to right. The spirally-shaped portion 4C is provided adjacent to the bending portion 52 on a distal end side of the flexible tubular portion 53. According to the present embodiment, a thrust generating section 6C is configured to be bendable using the spirally-shaped portion 4C and a covering 62 provided on the spirally-shaped portion 4C. The covering 62 is a covering member adapted to cover the spirally-shaped portion 4C. The covering 62 is configured to be an elastically deformable sheet made of fluoro rubber, urethane rubber, or the like and having predetermined elasticity and predetermined shape.

Since the bendable thrust generating section 6C made up of the spirally-shaped portion 4C and the covering 62 is provided on the flexible tubular portion 53, it becomes possible to prevent loss of flexibility in the flexible tubular portion 53.

An outer circumferential face on the distal end side of the flexible tubular portion 53 is provided with a front opening 58 and a rear opening 59 through which the flexible shaft 61 is passed. A straight line joining a center of the front opening 58 and a center of the rear opening 59 is disposed so as to be parallel to a longitudinal axis of the insertion portion 41 stretched into a linear shape.

Figure 17:
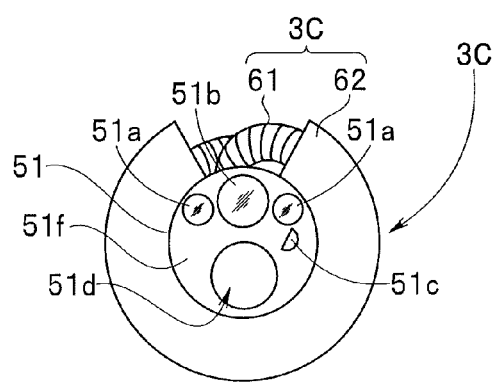

As shown in FIG. 17, the covering 62 is substantially C-shaped when viewed from the front and is placed in the insertion portion 41. A distal face of the distal end portion 51 of the insertion portion 41 is equipped, for example, with two illumination windows 51*a*, the observation window 51*b*, the nozzle 51*c*, and the distal end opening 51*d*.

Figure 20:
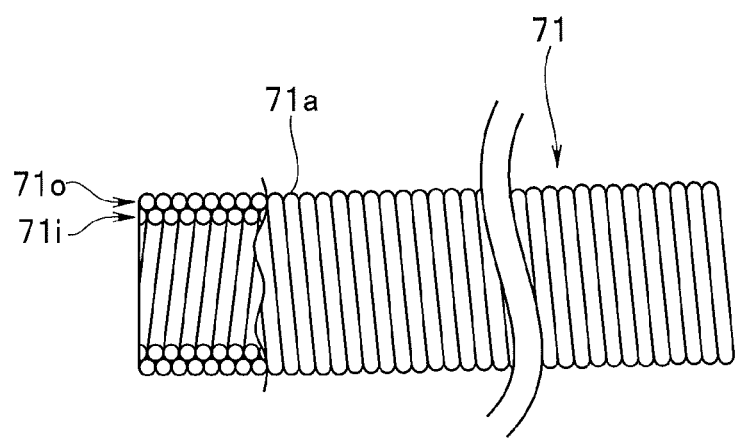
Figure 19:
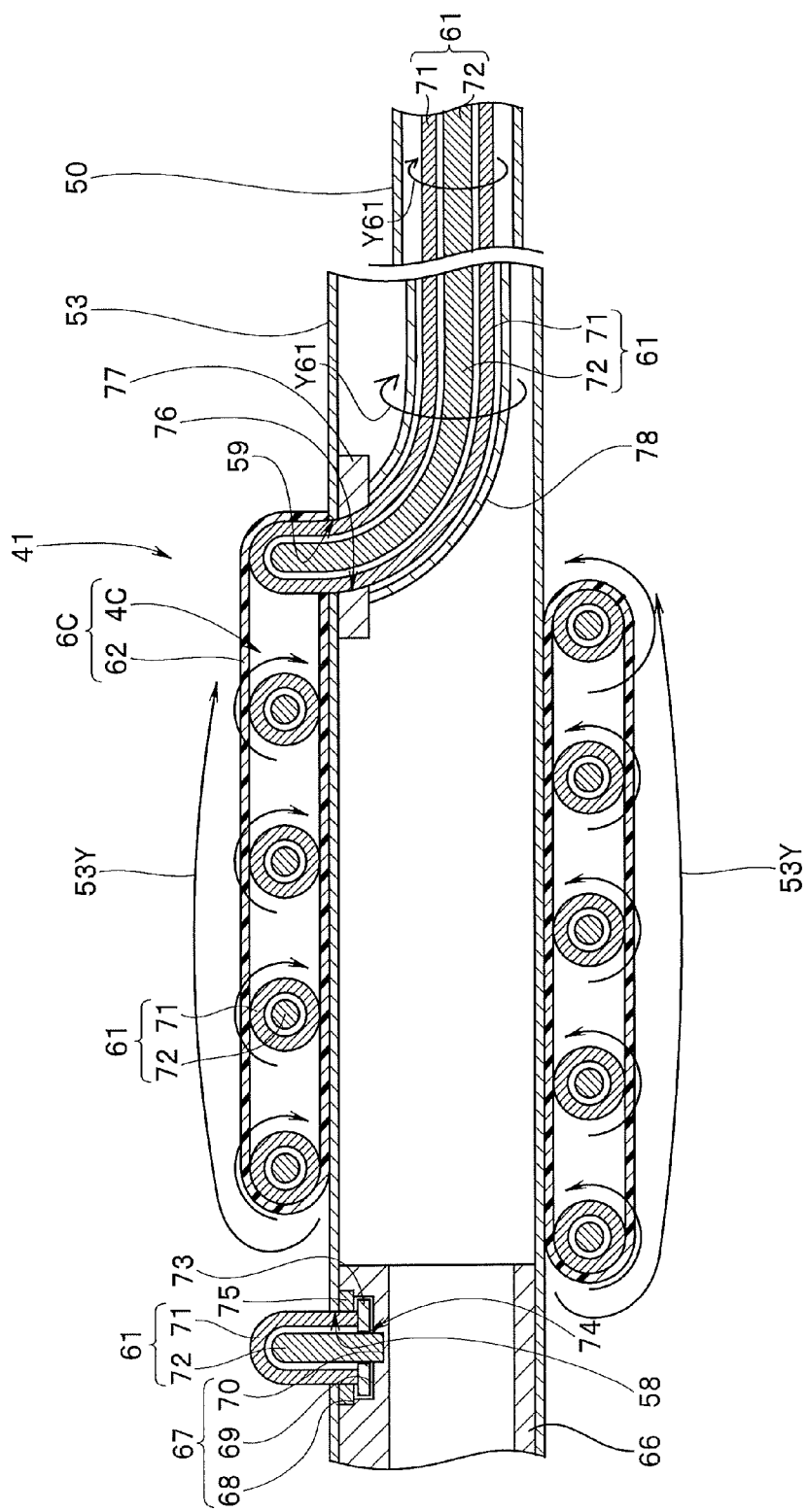

As shown in FIG. 19, the flexible shaft 61 includes a shaft body 71, which is a sheath, and a core wire 72. The shaft body 71 is configured as two close-wound layers of flexible non-stranded metal wires 71*a* made, for example, of stainless steel as shown in FIG. 20 to improve rotation transmission. The shaft body 71 has an inner layer 71*i* wound from right to left and an outer layer 71*o* wound from left to right.

Incidentally, the nonstranded metal wires of the shaft body 71 are not limited to stainless steel, and may be made of another metal such as tungsten wires, or a resin. Also, although the shaft body 71 has two layers in the present embodiment, the shaft body 71 may have three or four layers.

The core wire 72 is passed through the shaft body 71 in a loosely fitted state. The core wire 72 is made, for example, of stainless steel. The core wire 72 is capable of holding the spiral shape of the spirally-shaped portion 4C with the covering 62 disposed around the spirally-shaped portion 4C and is configured to be elastically deformable under external forces.

As shown in FIG. 19, on the distal end side, the flexible shaft 61 which forms the spirally-shaped portion 4C is disposed on a stepped hole 67 configured to communicate with the front opening 58. The stepped hole 67 is formed in a coupling member 66. The coupling member 66 is a coupling tube configured to couple the flexible tubular portion 53 and the bending portion 52 which make up the insertion portion 41 of the endoscope 42.

The stepped hole 67 is made up of a retention hole 68, a shaft distal end placement hole 69, and a core wire placement hole 70 starting from the distal end side. A shaft distal end member 73 is integrally fixed to a distal end face of the shaft body 71 of the flexible shaft 61 by joining such as soldering. The shaft distal end member 73 has a flat ring shape with a central through-hole 74, and outside diameter size of the shaft distal end member 73 is configured to be larger than diameter size of the shaft body 71.

The core wire 72 of the flexible shaft 61 is passed through the central through-hole 74 of the shaft distal end member 73. A distal end portion of the core wire 72 is placed in the core wire placement hole 70 and integrally fixed, for example, by gluing.

The shaft distal end member 73 which is a distal end of the flexible shaft 61 is placed in the shaft distal end placement hole 69. Being placed in this way, the shaft distal end member 73 is turnably mounted in the shaft distal end placement hole 69 by fixedly bonding a lid member 75 to the retention hole 68.

On the other hand, a proximal end side of the flexible shaft 61 which makes up the spirally-shaped portion 4C is introduced into the flexible tubular portion 53 through an intra-insertion portion communication hole 76 provided so as to communicate with the rear opening 59. The flexible shaft 61 introduced into the flexible tubular portion 53 is designed to be fixedly mounted to a coupling/fixing section 60 provided in the rotational driving device 46 by passing through the rotational driving force transmission tube 50 extending outward from the operation section 48 provided in the proximal end portion of the insertion portion 41.

The intra-insertion portion communication hole 76 is formed in a shaft introduction member 77 fixedly mounted near the rear opening 59. One opening of the intra-insertion portion communication hole 76 formed in the shaft introduction member 77 is placed in such a way as to communicate with the rear opening 59. On the other hand, a distal end portion of a shaft guide tube 78 is fixedly mounted to the other opening of the intra-insertion portion communication hole 76. A proximal end portion of the shaft guide tube 78 is fixedly mounted to the proximal end portion of the insertion portion 41.

That is, a proximal end of the flexible shaft 61 which forms the spirally-shaped portion 4C is designed to be led to the side of the operation section 48 by passing through the shaft guide tube 78 after passing the rear opening 59 and the intra-insertion portion communication hole 76.

Incidentally, although not illustrated, an air/water supply tube, a suction tube, an image pickup cable, a bending wire, and the like are passed through the insertion portion 41.

The covering 62 covers an inner surface of the spirally-shaped portion 4C, for example, from the proximal end to the distal end of the spirally-shaped portion 4C, and then after being turned to the side of an outer surface, covers the outer surface from the proximal end to the distal end. Then, end faces of belts are joined together by gluing or welding, and the belts are provided around the spirally-shaped portion 4C as the covering 62.

That is, the covering 62 covers substantially an entire circumference of the spirally-shaped portion 4C excluding an area 79 indicated by broken lines on opposite sides of 19Y-19Y line in FIG. 16. This provides a larger area of contact with luminal walls than when the belts 33 are arranged in the circumferential direction as described above.

Operation of the endoscope system 40 configured as described above will be described.

In the flexible tubular portion 53 of the insertion portion 41, the endoscope system 40 is equipped with the spirally-shaped portion 4C covered with the covering 62. The outside diameter of the flexible tubular portion 53 including the covering 62 is set to such a size as to allow the flexible tubular portion 53 to pass the anus smoothly. That is, the insertion portion 41 is inserted into the large intestine.

When inserting the insertion portion 41 into the large intestine, the surgeon inserts the distal end portion 51 of the insertion portion 41 gradually into the large intestine by gripping the insertion portion 41 with one hand and gripping the operation section 48 with the other hand.

Figure 21:
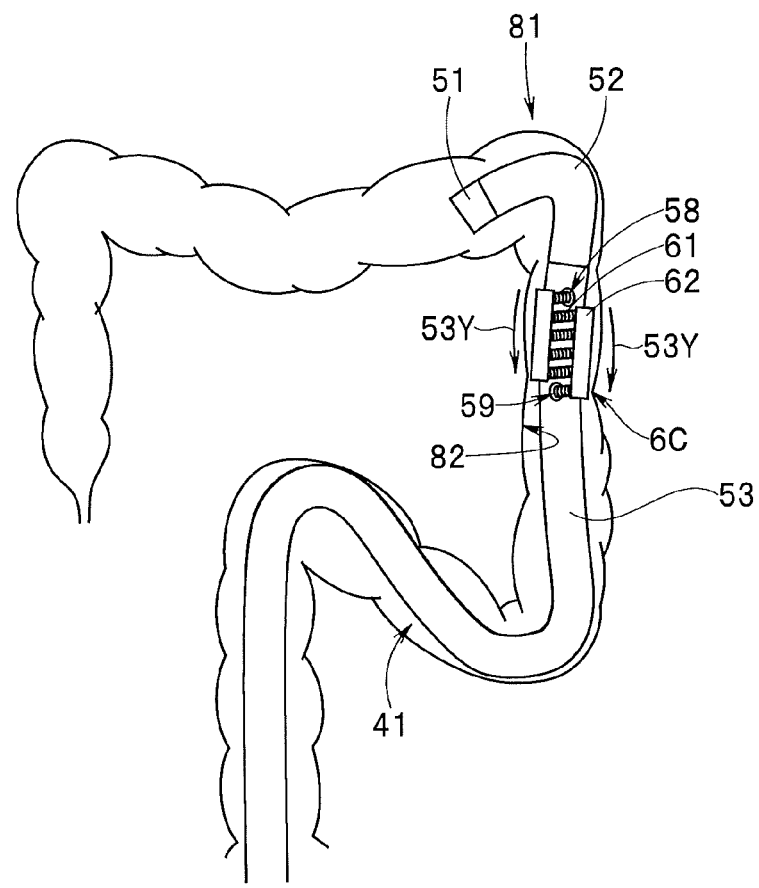

Then, when the distal end portion 51 of the insertion portion 41 reaches the splenic flexure 81 shown in FIG. 21, the surgeon performs the following operation to obtain thrust using the thrust generating section 6C.

First, upon confirming that the distal end portion 51 has reached the splenic flexure 81, the surgeon bends the bending portion 52 by operating the bending operation knob 54 and thereby hooks the distal end portion 51 onto the splenic flexure 81. In this state, the surgeon pushes in the insertion portion 41 from outside the body. However, with the bent bending portion 52 acting as resistance, the force exerted by the surgeon to push in the insertion portion 41 is difficult transmit to the distal end portion 51.

At this point, the surgeon turns on the pair of rotation motors 63 by flipping the operation switch 57 provided in the operation section 48. Consequently, the shaft body 71 of the flexible shaft 61 in the rotational driving force transmission tube 50 starts to rotate in a direction of arrow 61Y (see FIG. 19) along with rotation of the pair of gears 65.

Next, the rotation of the shaft body 71 is transmitted gradually to the distal end side through different parts of the shaft body 71, i.e., through the part passed through the insertion portion 41 and the part wound around the flexible tubular portion 53 configuring the spirally-shaped portion 4C. Then, the shaft distal end member 73 placed in the shaft distal end placement hole 69 of the stepped hole 67 enters a rotating state, putting the entire shaft body 71 into a rotating state. Subsequently, as the rotation of the rotation motors 63 is continued, the shaft body 71 continues rotating.

In so doing, as shown in FIG. 19, that part of the shaft body 71 which is located on the top surface of the flexible tubular portion 53 rotates clockwise around an axis perpendicular to the plane of the paper. On the other hand, that part of the shaft body 71 which is located on the undersurface of the flexible tubular portion 53 rotates counterclockwise around the axis perpendicular to the plane of the paper.

The shaft body 71 makes up the spirally-shaped portion 4C by being placed in such a way as to spiral around the flexible tubular portion 53. Consequently, a rotation axis of the shaft body 71 is positioned so as to be substantially orthogonal to an insertion direction of the insertion portion 41. That is, the shaft body 71 is wound in such a way that a shaft axis of the shaft body 71 will be substantially orthogonal to the insertion direction on an outer circumferential face of the flexible tubular portion 53.

Therefore, the axial rotation of the shaft body 71 in the insertion portion 41 and the like is performed around the rotation axis substantially orthogonal to the insertion direction on the outer circumferential face of the flexible tubular portion 53. The shaft axis is a longitudinal central axis of the shaft body 71.

Figure 22:
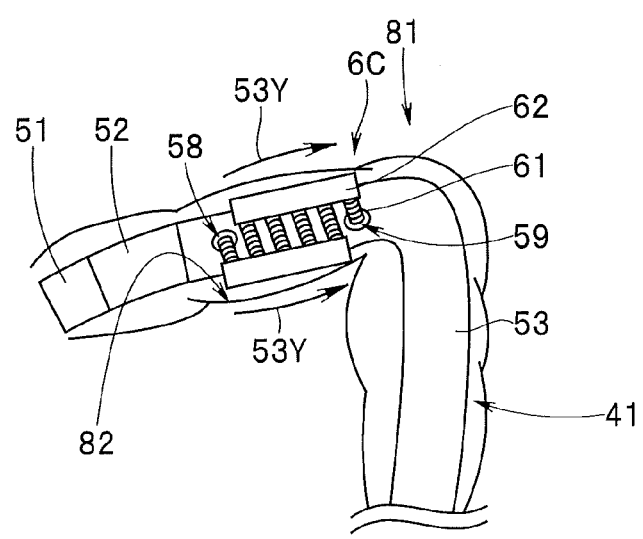

Consequently, the covering 62, which is placed in contact with the shaft body 71, rotates as indicated by arrow 53Y in FIGS. 19 and 21. As the covering 62 rotates, a frictional force is generated between large intestine walls 82 and the covering 62. With the frictional force acting as the thrust used to advance the insertion portion 41 into deep part, the distal end side of the flexible tubular portion 53 passes the splenic flexure 81 as shown in FIG. 22.

In this way, the thrust generating section 6C is configured by forming the spirally-shaped portion 4C on the distal end side of the flexible tubular portion 53 which makes up the insertion portion 41 of the endoscope 42 and placing the covering 62 in contact with the spirally-shaped portion 4C. Consequently, by turning the shaft body 71 of the flexible shaft 61 which makes up the spirally-shaped portion 4C, the covering 62 which covers the spirally-shaped portion 4C can be rotated clockwise or counterclockwise.

Then, as the covering 62 which covers the spirally-shaped portion 4C is placed in contact with the large intestine walls 82, the rotation of the covering 62 provides the thrust used to advance or retract the insertion portion 41.

The use of the covering 62 to cover the spirally-shaped portion 4C provides a larger area of contact with the walls than when the ring-shaped belts 33 are used, and thereby makes thrust readily available.

The rest of the operation and other advantages are the same as those of the embodiments described above.

Incidentally, if the shaft body 71 is rotated in a direction opposite to the direction of arrow 18Y by rotating the pair of rotation motors 63 in an opposite direction, that part of the shaft body 71 which is located on the top surface of the flexible tubular portion 53 in FIG. 19 rotates counterclockwise around an axis perpendicular to the plane of the paper and that part of the shaft body 71 which is located on the undersurface of the flexible tubular portion 53 rotates clockwise around the axis perpendicular to the plane of the paper.

Also, if the flexible shaft 61 of the spirally-shaped portion 4C is wound from right to left, rotating the shaft body 71 in the direction opposite to the direction of arrow 18Y provides the thrust used to advance the insertion portion 41.

Furthermore, the thrust generating mechanism section 3C is made up of the rotational driving device 46 which is an outside apparatus as well as components provided in the flexible tubular portion 53, including the spirally-shaped portion 4C formed by the flexible shaft 61 and the covering 62 which covers the spirally-shaped portion 4C. This makes it possible to include parts and the like used to switch the rotational direction of the covering 62 in the outside apparatus and thereby prevent increases in the diameter of the insertion portion 41.

Figure 23:
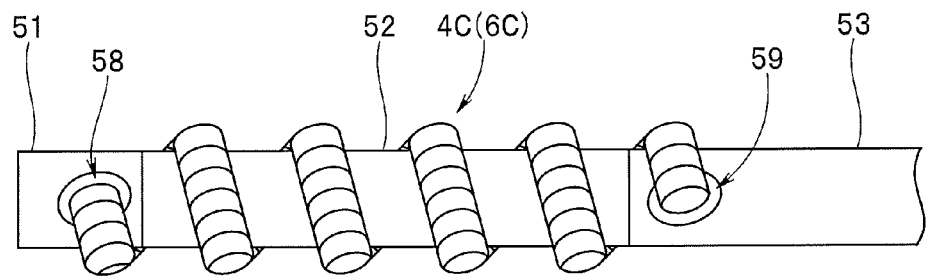
FIG. 23 is a diagram illustrating an exemplary configuration of the insertion portion whose bending portion is provided with the thrust developed by the thrust generating section.

According to the present embodiment, the thrust generating section 6C is provided on the distal end side of the flexible tubular portion 53 which makes up the insertion portion 41. However, since the thrust generating section 6C is configured to be bendable using the spirally-shaped portion 4C and the covering 62 provided on the spirally-shaped portion 4C, the thrust generating section 6C made up of the spirally-shaped portion 4C and a covering (not shown) may be provided in the bending portion 52 as shown in FIG. 23.

In this configuration, the front opening 58 which allows passage of the flexible shaft 61 is provided in the distal end portion 51 and the rear opening 59 is provided in the bending portion 52 or the flexible tubular portion 53. Then, a stepped hole (not shown) is formed in a distal rigid member (not shown) in such a way as to communicate with the front opening 58, where the distal rigid member makes up the distal end portion 51 which is coupled to the bending pieces which make up the bending portion 52.

On the other hand, the intra-insertion portion communication hole is provided in a coupling member (not shown) which couples the flexible tubular portion 53 and the bending portion 52, so as to communicate between the coupling member and the rear opening 59.

Figure 24:
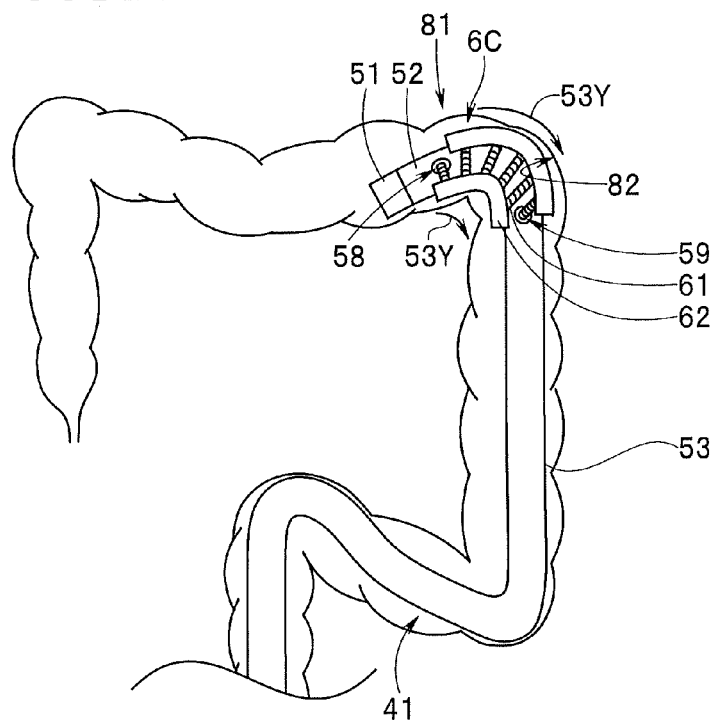
FIG. 24 is a diagram illustrating operation of the insertion portion whose bending portion is equipped with the thrust generating section made up of the flexible shaft covered with the spirally-shaped portion covering.

If the thrust generating section 6C is provided in the bending portion 52 in this way, when the distal end portion 51 of the insertion portion 41 reaches the splenic flexure 81, by operating the bending operation knob 54, the surgeon can bend the bending portion 52 equipped with the thrust generating section 6C as shown in FIG. 24 and thereby hook the distal end portion 51 onto the splenic flexure 81.

Figure 25:
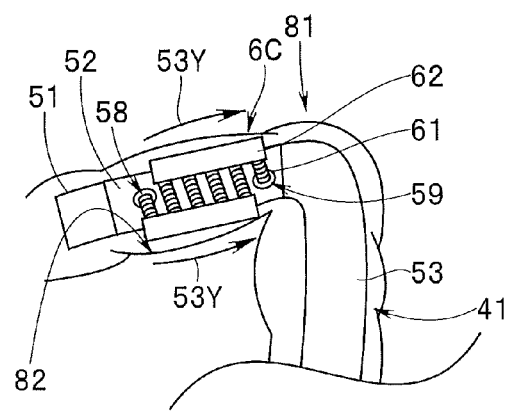
FIG. 25 is a diagram illustrating how the insertion portion has passed the splenic flexure by means of thrust developed by the thrust generating section provided in the bending portion.

In this state, as the surgeon turns on the pair of rotation motors 63 by flipping the operation switch 57 of the operation section 48, the covering 62 rotates as indicated by arrow 53Y in FIG. 24. When the covering 62 is rotated, a frictional force is generated between the large intestine walls 82 and the covering 62. With the frictional force acting as the thrust used to advance the insertion portion 41 into deep part, the insertion portion 41 passes the splenic flexure 81 as shown in FIG. 25.

In this way, if the thrust generating section 6C is provided in the bending portion 52, the thrust generating section 6C can be placed further on the distal end side of the insertion portion 41, making it possible to obtain thrust used to advance the insertion portion 41 more efficiently.

A variation of the thrust generating mechanism section will be described with reference to FIG. 26.

The thrust generating mechanism section in FIG. 26 is configured similarly to the fourth embodiment in terms of the thrust generating section 6C, but differs in an internal configuration of the rotational driving device 46. The rotational driving device 46 includes a rotational driving unit 90 and a driving unit advance/retract device 91.

The rotational driving unit 90 is configured by integrally fixing the pair of rotation motors 63 and the like to a boxlike body 92. The boxlike body 92 can freely advance and retract in an extending direction of the flexible shaft in the rotational driving device 46. The driving unit advance/retract device 91 is equipped, for example, with a rack and pinion mechanism adapted to advance and retract the boxlike body 92. An advance/retract motor (not shown) of the rack and pinion mechanism is integrally fixed to the rotational driving device 46.

According to the present embodiment, a tooth portion provided on a motor shaft is rotated by the advance/retract motor provided in the driving unit advance/retract device 91. Consequently, along with the rotation of the tooth portion, the rack meshed with the tooth portion advances, causing the boxlike body 92 of the rotational driving unit 90 to move toward the distal end side by a distance L in the rotational driving device 46.

As the boxlike body 92 of the rotational driving unit 90 moves toward the distal end side by a distance L, the flexible shaft 61 passed through the rotational driving force transmission tube 50 and the flexible tubular portion 53 is moved as well. That is, the flexible shaft 61 is pushed out of the rear opening 59.

If, for example, the spiral of a spirally-shaped portion 4D of a thrust generating mechanism section 3D provided around the flexible tubular portion 53 has five turns and the outside diameter size of each turn is $\phi D$, circumferential length of each turn is $\pi D$ and a sum of the circumferential lengths of the spirally-shaped portion 4D is $5\pi D$.

Thus, when the boxlike body 92 of the rotational driving unit 90 is moved by the distance L toward the distal end side in the rotational driving device 46 and the flexible shaft 61 is pushed outward by L from the rear opening 59, the sum of the circumferential lengths changes from $5\pi D$ to $5\pi D + L$. Consequently, the outside diameter of each turn of the spiral changes from $\phi D$ to $(\phi D + L/5\pi)$. That is each turn of the spiral is increased by $L/5\pi$ in outside diameter.

Then, when the boxlike body 92 of the rotational driving unit 90 is moved to the original position, the outside diameter of the spiral of a spirally-shaped portion 4D returns to $\phi D$.

In this way, the advanceable/retractable rotational driving unit 90 is provided in the rotational driving device 46, the driving unit advance/retract device 91 is provided to advance and retract the rotational driving unit 90, and the placement location of the rotational driving unit 90 is changed by operating the driving unit advance/retract device 91 as required. This makes it possible to change the outside diameter size of the spirally-shaped portion 4D as required according to the inside diameter of the lumen by pushing the flexible shaft 61 out of the rear opening 59 and thereby obtain thrust efficiently.

Therefore, even if there is a difference between the inside diameter of the lumen and the outside diameter of the spiral of the spirally-shaped portion 4D due to individual differences or observed sites, observations can be carried out properly by adjusting the outside diameter of the spirally-shaped portion 4D to the inside diameter of the lumen.

Although the intraductal insertion device is a medical instrument in the embodiments described above, the intraductal insertion device is not limited to medical instruments, and may be an instrument used to inspect piping in a factory, i.e., an instrument other than medical instruments.

It should be understood that the present invention is not limited to the embodiments described above and that various modifications may be made without departing from the spirit and scope of the invention.

What is claimed is:

1. An intraductal insertion device comprising a thrust generating section installed at an insertion portion, wherein:
   the thrust generating section includes a flexible shaft having one end portion and an other end portion, the flexible shaft being wound around an outer circumferential face of the insertion portion and adapted to rotate clockwise or counterclockwise around a shaft axis; and
   a driving section adapted to impart a rotational force to rotate the flexible shaft around the shaft axis;
   wherein the one end portion of the flexible shaft is placed in the insertion portion rotatably around the shaft so as to be prevented from falling off, and the other end portion of the flexible shaft wound around the insertion portion extends in a proximal direction of the insertion portion and is connected to the driving section;
   the insertion portion has a first hole and a second hole on a same circumference of an outer circumferential face, where the first hole communicates between the insertion portion and the outside and a distal end side of the flexible shaft is turnably placed in the second hole; and the thrust generating section is configured by placing, in the second hole, the flexible shaft led out of a through-hole in the insertion portion via the first hole and thereby winding the flexible shaft at least half a turn or more around the outer circumferential face of the insertion portion.

2. The intraductal insertion device according to claim 1, wherein:

the first hole and the second hole are spaced away from each other in a longitudinal direction of the insertion portion; and the thrust generating section is a spirally-shaped portion configured by placing, in the second hole, the flexible shaft led out of a through-hole in the insertion portion via the first hole and thereby winding the flexible shaft spirally around the outer circumferential face of the insertion portion.

3. The intraductal insertion device according to claim 2, wherein:

the thrust generating section includes the spirally-shaped portion and a covering member having predetermined elasticity and predetermined shape and adapted to cover an inner surface side and an outer surface side of the spirally-shaped portion.

4. The intraductal insertion device according to claim 3, wherein the covering member is made up of a plurality of ring-shaped belts disposed in a circumferential direction so as to cover an outer circumferential face of the spirally-shaped portion.

5. The intraductal insertion device according to claim 3, wherein the covering member is a covering provided at the spirally-shaped portion by being placed in the shape of the letter C with respect to the insertion portion.

6. The intraductal insertion device according to claim 1, wherein a circumferential shaft groove whose depth has been set to a predetermined size is formed in the outer circumferential face of the insertion portion to place the flexible shaft.

7. The intraductal insertion device according to claim 1, wherein:

the intraductal insertion device is an insertion aid equipped with a hollow portion in a longitudinal direction; and the thrust generating section is configured by spirally winding the flexible shaft around an axis of the hollow portion, the flexible shaft being adapted to rotate clockwise or counterclockwise around the shaft axis.

8. The intraductal insertion device according to claim 1, wherein:

the intraductal insertion device is a capsule endoscope made up of a capsule which includes a capsule body provided with the first hole and a circumferentially rotating capsule section provided with the second hole and mounted on an open side of the capsule body so as to rotate clockwise and counterclockwise;

the capsule contains a shaft rotation motor adapted to rotate the flexible shaft clockwise and counterclockwise around the shaft axis and a circumferentially rotating capsule section rotation motor adapted to rotate the circumferentially rotating capsule section clockwise and counterclockwise; and the thrust generating section is a spirally-shaped portion configured by leading the flexible shaft fixed to the shaft rotation motor to the outside via the first hole, placing the flexible shaft in the second hole, and thereby winding the flexible shaft spirally around an outer circumferential face of a trunk portion of the capsule.

9. The intraductal insertion device according to claim 1, wherein:

the intraductal insertion device is an endoscope equipped with the insertion portion made up of a distal end portion, a bending portion, and a flexible tubular portion installed consecutively starting from a distal end side as well as with a front opening and a rear opening disposed so as to be parallel to a longitudinal axis of the insertion portion, where a distal end side of the flexible shaft is turnably placed in the front opening and the rear opening communicates between the insertion portion and the outside; and the thrust generating section comprises:

a spirally-shaped portion wound around the outer circumferential face of the insertion portion between the front opening and the rear opening, and a covering member having predetermined elasticity and predetermined shape and adapted to cover an inner surface side and an outer surface side of the spirally-shaped portion.

10. The intraductal insertion device according to claim 9, wherein:

the endoscope comprises, as an outside apparatus of the endoscope, a rotational driving device equipped with a driving unit adapted to rotate the flexible shaft; and the driving unit of the rotational driving device is configured to freely advance and retract in an extending direction of the flexible shaft by means of a driving unit advance/retract device and adapted to push the flexible shaft out of a rear hole when advanced.

11. The intraductal insertion device according to claim 1, wherein the flexible shaft has a double-layer structure made up of a central body and a hollow sheath turnably mounted around an outside of the central body.

* * * * *